(12) United States Patent
Fielder et al.

(10) Patent No.: US 10,596,362 B2
(45) Date of Patent: *Mar. 24, 2020

(54) PERCUTANEOUS DRUG DELIVERY APPARATUS

(71) Applicant: RENISHAW (IRELAND) LIMITED, Swords (IE)

(72) Inventors: Paul David Fielder, Chalford Hill (GB); Steven S Gill, Bristol (GB); Trefor Owen Lewis, Bristol (GB); Andrew Samuel Vick, Sidmouth (GB)

(73) Assignee: RENISHAW (IRELAND) LIMITED, Wotton-under-Edge (GB)

( * ) Notice: Subject to any disclaimer, the term of this patent is extended or adjusted under 35 U.S.C. 154(b) by 57 days.

This patent is subject to a terminal disclaimer.

(21) Appl. No.: 14/445,626

(22) Filed: Jul. 29, 2014

(65) Prior Publication Data

US 2014/0343500 A1   Nov. 20, 2014

Related U.S. Application Data

(63) Continuation of application No. 13/575,769, filed as application No. PCT/GB2011/000183 on Feb. 11, 2011, now Pat. No. 8,827,987.

(30) Foreign Application Priority Data

Feb. 12, 2010   (GB) .................................. 1002370.3

(51) Int. Cl.
*A61M 39/02*   (2006.01)
*A61B 17/17*   (2006.01)

(52) U.S. Cl.
CPC ..... *A61M 39/0247* (2013.01); *A61B 17/1739* (2013.01); *A61M 2039/0261* (2013.01);
(Continued)

(58) Field of Classification Search
CPC ...... A61B 17/1739; A61M 2039/0261; A61M 2039/0276; A61M 2039/0282;
(Continued)

(56) References Cited

U.S. PATENT DOCUMENTS 4,013,074 A   3/1977   Siposs
4,511,355 A   4/1985   Franetzki et al.
(Continued)

FOREIGN PATENT DOCUMENTS

CN   2684843 Y   3/2005
CN   2834581 Y   11/2006
(Continued)

OTHER PUBLICATIONS

Chinese Office Action issued in Chinese Patent Application No. 201180009336.9 dated Mar. 3, 2014 (w/ translation).
(Continued)

*Primary Examiner* — Quynh-Nhu H. Vu
(74) *Attorney, Agent, or Firm* — Oliff PLC

(57) ABSTRACT

An implantable percutaneous fluid delivery device is described that includes a subcutaneous base portion having one or more ports for supplying fluid to one or more implanted catheter devices and a percutaneous portion including an extracorporeal surface. The one or more ports of the subcutaneous base portion are accessible from the extracorporeal surface of the percutaneous portion. The subcutaneous base portion is at least partially insertable into a complementary recess formed in a bone, the subcutaneous base portion including one or more features for gripping the internal surface of such a complementary recess thereby directly anchoring the subcutaneous base portion to the bone. The device may be used to route fluid to neurosurgical catheters optionally via a router unit.

18 Claims, 10 Drawing Sheets

(52) U.S. Cl.
CPC ............... *A61M 2039/0276* (2013.01); *A61M 2039/0282* (2013.01); *A61M 2205/02* (2013.01); *A61M 2205/7518* (2013.01); *A61M 2210/0687* (2013.01)

(58) Field of Classification Search
CPC .. A61M 2039/1083; A61M 2039/1088; A61M 2210/0687; A61M 39/0247; A61M 2039/025; A61M 39/105; A61M 5/14276
See application file for complete search history.

(56) References Cited

U.S. PATENT DOCUMENTS

| | | | |
|---|---|---|---|
| 4,578,063 A | | 3/1986 | Inman et al. |
| 4,634,422 A | | 1/1987 | Kantrowitz et al. |
| 4,692,147 A | | 9/1987 | Duggan |
| 4,695,273 A | | 9/1987 | Brown |
| 4,705,464 A | | 11/1987 | Arimond |
| 4,772,263 A | | 9/1988 | Dorman et al. |
| 4,790,826 A | | 12/1988 | Elftman |
| 4,822,339 A | | 4/1989 | Tran |
| 4,897,081 A | | 1/1990 | Poirier et al. |
| 4,903,707 A | | 2/1990 | Knute et al. |
| 5,098,397 A | | 3/1992 | Svensson et al. |
| 5,120,313 A | | 6/1992 | Elftman |
| 5,122,114 A | * | 6/1992 | Miller ............... A61M 39/0208 604/175 |
| 5,171,216 A | | 12/1992 | Dasse et al. |
| 5,221,474 A | | 6/1993 | Yokono et al. |
| 5,318,545 A | * | 6/1994 | Tucker ................ A61L 29/02 604/244 |
| 5,352,207 A | | 10/1994 | Nussbaum |
| 5,549,581 A | | 8/1996 | Lurie et al. |
| 5,752,930 A | | 5/1998 | Rise et al. |
| 5,782,645 A | | 7/1998 | Stobie et al. |
| 5,833,655 A | | 11/1998 | Freed et al. |
| 5,836,935 A | * | 11/1998 | Ashton ................ A61K 9/0024 424/424 |
| 5,906,596 A | | 5/1999 | Tallarida |
| 5,916,200 A | | 6/1999 | Eppley et al. |
| 5,954,687 A | * | 9/1999 | Baudino ............. A61M 25/02 604/174 |
| 5,990,382 A | | 11/1999 | Fox |
| 6,018,094 A | | 1/2000 | Fox |
| 6,044,304 A | | 3/2000 | Baudino |
| 6,086,555 A | | 7/2000 | Eliasen et al. |
| 6,134,477 A | | 10/2000 | Knuteson |
| 6,152,933 A | * | 11/2000 | Werp ................. A61M 27/006 604/165.01 |
| 6,347,711 B1 | | 2/2002 | Goebel et al. |
| 6,356,792 B1 | * | 3/2002 | Errico ................. A61N 1/0534 606/129 |
| 6,454,774 B1 | | 9/2002 | Fleckenstein |
| 6,471,689 B1 | * | 10/2002 | Joseph ................. A61L 29/04 424/424 |
| 6,607,504 B2 | | 8/2003 | Haarala et al. |
| 6,609,020 B2 | | 8/2003 | Gill |
| 6,685,674 B2 | * | 2/2004 | Douglas .............. A61M 5/158 604/167.05 |
| 6,758,841 B2 | | 7/2004 | Haarala et al. |
| 6,840,919 B1 | * | 1/2005 | Håkansson ....... A61M 39/0247 439/39 |
| 6,852,106 B2 | | 2/2005 | Watson et al. |
| 7,331,940 B2 | | 2/2008 | Sommerich |
| 7,604,658 B2 | * | 10/2009 | Wilson ................ A61B 5/031 606/304 |
| 7,833,204 B2 | | 11/2010 | Picha |
| 8,323,270 B2 | | 12/2012 | Shachar et al. |
| 8,827,987 B2 | * | 9/2014 | Fielder .............. A61M 5/14276 604/175 |
| 8,974,422 B2 | | 3/2015 | Gill et al. |
| 9,439,774 B2 | | 9/2016 | de Villiers et al. |
| 2002/0133232 A1 | * | 9/2002 | Ricci ................... A61B 17/68 623/23.5 |
| 2003/0004520 A1 | | 1/2003 | Haarala et al. |
| 2003/0023208 A1 | | 1/2003 | Osypka et al. |
| 2003/0120215 A1 | | 6/2003 | Bousquet |
| 2003/0130577 A1 | | 7/2003 | Purdy et al. |
| 2003/0171711 A1 | | 9/2003 | Rohr et al. |
| 2003/0171738 A1 | | 9/2003 | Konieczynski et al. |
| 2004/0034367 A1 | | 2/2004 | Malinowski |
| 2004/0243064 A1 | | 12/2004 | Sommerich |
| 2004/0249361 A1 | | 12/2004 | Denoth et al. |
| 2004/0260361 A1 | | 12/2004 | Gibson |
| 2004/0267238 A1 | | 12/2004 | Haarala et al. |
| 2005/0075624 A1 | | 4/2005 | Miesel |
| 2005/0143800 A1 | | 6/2005 | Lando et al. |
| 2005/0182420 A1 | | 8/2005 | Schulte et al. |
| 2005/0203486 A1 | | 9/2005 | Sommerich |
| 2005/0245887 A1 | | 11/2005 | Olsen et al. |
| 2005/0267591 A1 | * | 12/2005 | Ricci ................. A61M 39/0247 623/23.44 |
| 2005/0283203 A1 | | 12/2005 | Flaherty et al. |
| 2006/0122578 A1 | * | 6/2006 | Lord ................. A61M 5/14224 604/891.1 |
| 2007/0255262 A1 | | 11/2007 | Haase |
| 2008/0287910 A1 | | 11/2008 | Picha |
| 2009/0030373 A1 | | 1/2009 | Gill |
| 2009/0082758 A1 | * | 3/2009 | Gill ................... A61M 5/14276 604/891.1 |
| 2009/0187149 A1 | | 7/2009 | Nelson |
| 2009/0227989 A1 | | 9/2009 | Burke et al. |
| 2010/0042070 A1 | * | 2/2010 | Gill ................... A61M 39/0247 604/513 |
| 2010/0069892 A1 | | 3/2010 | Steinbach et al. |
| 2010/0145162 A1 | * | 6/2010 | Devauchelle ........ A61N 1/0529 600/300 |
| 2010/0217236 A1 | * | 8/2010 | Gill ...................... A61L 31/028 604/528 |
| 2012/0310182 A1 | | 12/2012 | Fielder et al. |
| 2014/0343500 A1 | | 11/2014 | Fielder et al. |
| 2014/0371679 A1 | | 12/2014 | Woolley et al. |

FOREIGN PATENT DOCUMENTS

| | | | |
|---|---|---|---|
| CN | 201088751 Y | | 7/2008 |
| CN | 101384286 A | | 3/2009 |
| CN | 101400386 A | | 4/2009 |
| CN | 101537224 A | | 9/2009 |
| CN | 101541356 A | | 9/2009 |
| DE | 20115120 U1 | | 3/2002 |
| DE | 10143820 A1 | | 3/2003 |
| EP | 0266243 A1 | | 5/1988 |
| EP | 0 992 257 A1 | | 4/2000 |
| EP | 1426074 A1 | | 6/2004 |
| EP | 1 481 697 A1 | | 12/2004 |
| EP | 1576975 A1 | | 9/2005 |
| EP | 1704891 B1 | | 6/2011 |
| FR | 2690625 A1 | | 11/1993 |
| FR | 2750054 A1 | | 12/1997 |
| GB | 2389791 A | | 12/2003 |
| GB | WO2007093778 | * | 8/2007 ............ A61M 5/142 |
| GB | 2459101 A | | 10/2009 |
| JP | S48-5290 A | | 1/1973 |
| JP | S62-240069 A | | 10/1987 |
| JP | H02-168968 A | | 6/1990 |
| JP | H03-126438 | | 5/1991 |
| JP | H03-286776 A | | 12/1991 |
| JP | H05-42220 A | | 2/1993 |
| JP | H08-141088 A | | 6/1996 |
| JP | H11-504231 A | | 4/1999 |
| JP | 2001-505115 A | | 4/2001 |
| JP | 2001-509063 A | | 7/2001 |
| JP | 2004-000495 A | | 1/2004 |
| JP | 2006-520656 A | | 9/2006 |
| JP | 2006-263470 A | | 10/2006 |
| JP | 2006-525827 A | | 11/2006 |
| JP | 2009-526589 A | | 7/2009 |
| JP | 2009-219889 A | | 10/2009 |
| WO | WO 89/07467 A1 | | 8/1989 |
| WO | 96/29953 A1 | | 10/1996 |
| WO | WO 97/49438 A1 | | 12/1997 |

(56) References Cited

FOREIGN PATENT DOCUMENTS

| WO | 98/31417 A2 | 7/1998 | | |
|---|---|---|---|---|
| WO | WO 99/34754 A1 | 7/1999 | | |
| WO | WO 01/12158 A1 | 2/2001 | | |
| WO | WO 03/077784 A1 | 9/2003 | | |
| WO | WO 03/077785 A1 | 9/2003 | | |
| WO | 2004/084768 A2 | 10/2004 | | |
| WO | WO 2004/105839 A1 | 12/2004 | | |
| WO | WO 2007/093778 A1 | 8/2007 | | |
| WO | WO 2007/104953 A1 | 9/2007 | | |
| WO | WO 2007/104961 A1 | 9/2007 | | |
| WO | WO 2008/062173 A1 | 5/2008 | | |
| WO | WO2008062173 | * | 5/2008 | ............ A61M 1/00 |
| WO | WO 2009/047494 A1 | 4/2009 | | |
| WO | 2009/094389 A1 | 7/2009 | | |
| WO | WO 2009/094389 A1 | 7/2009 | | |
| WO | 2009/103758 A2 | 8/2009 | | |
| WO | WO 2009/096851 A1 | 8/2009 | | |
| WO | WO 2009/128959 A1 | 10/2009 | | |
| WO | WO 2011/098769 A1 | 8/2011 | | |

OTHER PUBLICATIONS

Jun. 30, 2011 Search Report issued in PCT/GB2011/000183.
Jun. 30, 2011 Search Report issued in PCT/GB2011/000182.
Fielder et al; U.S. Appl. No. 13/575,759, filed Jul. 27, 2012.
May 21, 2010 Search Report issued in Patent Application No. GB1002370.3.
"Linear Incision Technique—Procedure and clinical results," BAHA Clinical Review.
N.K.O. & Hoofd-Halsheelkunde, "Bone Anchored Hearing Aids (B.A.H.A.)," http://www.nko.uza.be/prof/baha/index.html, Oct. 11, 2008, 5 pages.
Borenstein, Jeffrey T., "Medicine by Micromachine," IEEE Spectrum, Nov. 2009, Int, pp. 35-39.
Bovo, R., "Simplified technique without skin flap for the bone-anchored hearing aid (BAHA) implant," Technical Note, ACTA Otorhinolaryngologica Italica 2008;28, pp. 252-255, Ferrara, Italy.
Jul. 25, 2013 Office Action issued in Chinese Patent Application No. 201180009336.9 (with translation).
Aug. 16, 2013 Office Action issued in Chinese Patent Application No. 201180009002.1 (with translation).
Jun. 23, 2014 Office Action issued in Chinese Patent Application No. 201180009002.1 (with translation).
Feb. 25, 2015 Office Action issued in Chinese Application No. 201180009002.1.
Dec. 11, 2015 Search Report issued in European Application No. 15 18 1867.
Nov. 14, 2014 Office Action issued in Japanese Application No. 2012-552462.
Jun. 30, 2011 Written Opinion of International Search Report issued in PCT/GB2011/000183.
Jun. 30, 2011 Written Opinion of International Search Report issued in PCT/GB2011/000182.
Lundgren et al. "Soft-Tissue-Anchored Percutaneous Device for Long-Term Intracorporeal Access." Journal of Investigative Surgery. vol. 2, pp. 17-27.1989.
Fricova et al. "The Implantable Intravenous Ports". Bolest. 2006. pp. 165-172.
Nyman et al. "Soft-Tissue-Anchored Transcutaneous Port for Long-Term Percutaneous Transhepatic Biliary Drainage". CardioVascular and Interventional Radiology. vol. 28, pp. 53-59. 2005.
Berntorp et al. "Experience with a new percutaneous port system, Percuseal, for intravenous injection in patients with haemophilia, von Willebrand disease and severe alpha.sub.1-antitrypsin deficiency". Haemophilia. vol. 9, pp. 173-178. 2003.
Germano et al. "Surgical Techniques for Stereotactic Implant of Deep Brain Stimulators". Seminars in Neurosurgery. vol. 12, No. 2, pp. 213-223. 2001.

"Lead Kit for Deep Brain Stimulation". Medtronic Manual, pp. 9-56. 2002.
May 6, 2013 Chinese Office Action issued in Application No. 201210084254.7.
Jul. 6, 2012 Office Action issued in Japanese Patent Application No. 2009-537691.
Mar. 25, 2014 Office Action issued in Chinese Application No. 201210084254.7.
Sep. 20, 2013 Office Action issued in Japanese Application No. 2009-537691.
Dec. 12, 2014 Office Action issued in Canadian Application No. 2,670,164.
Nov. 15, 2014 Office Action issued in Chinese Application No. 201210084254.7.
Oct. 18, 2013 Office Action issued in U.S. Appl. No. 13/575,769.
Feb. 24, 2014 Office Action issued in U.S. Appl. No. 13/575,769.
U.S. Appl. No. 14/581,549, filed Dec. 23, 2014 in the name of Gill et al.
U.S. Appl. No. 14/431,133, filed Mar. 25, 2015 in the name of Woolley et al.
May 9, 2014 Office Action issued in U.S. Appl. No. 12/312,584.
Dec. 18, 2013 Office Action issued in U.S. Appl. No. 12/312,584.
Aug. 10, 2011 Office Action issued in U.S. Appl. No. 12/312,584.
Dec. 6, 2010 Office Action issued in U.S. Appl. No. 12/312,584.
Apr. 4, 2008 International Search Report issued in International Patent Application No. PCT/GB2007/004438.
Jan. 31, 2014 International Search Report issued in International Patent Application No. PCT/GB2013/052559.
Dec. 31, 2012 Search Report issued in GB Patent Application No. 1217606.01.
Jan. 31, 2014 Written Opinion of International Search Report issued in International Patent Application No. PCT/GB2013/052559.
Apr. 4, 2008 Written Opinion of International Search Report Issued in PCT/GB2007/004438.
Jul. 1, 2015 Office Action issued in Chinese Application No. 201210084254.7.
Jul. 31, 2015 Office Action issued in U.S. Appl. No. 13/575,759.
Oct. 9, 2014 Office Action issued in Japanese Application No. 2012-552463.
Jun. 22, 2016 Office Action issued in U.S. Appl. No. 14/431,133.
Jun. 17, 2016 Office Action issued in U.S. Appl. No. 13/575,759.
May 2, 2016 Office Action issued in Japanese Application No. 2015-166782.
May 17, 2016 Office Action issued in European Application No. 11 706 9005.
May 13, 2016 Office Action issued in Chinese Application No. 201210084254.7.
Jul. 20, 2016 Office Action issued in Chinese Patent Application No. 201380051627.3.
Nov. 4, 2016 Office Action issued in Chinese Patent Application No. 201410772721.4.
Mar. 14, 2017 Office Action Issued in U.S. Appl. No. 13/575,759.
Mar. 14, 2017 Office Action issued in U.S. Appl. No. 14/581,549.
Oct. 26, 2016 Office Action issued in Application No. 201210084254.7.
Aug. 23, 2017 Office Action issued in U.S. Appl. No. 13/575,759.
Aug. 28, 2017 Office Action issued in U.S. Appl. No. 14/581,549.
May 17, 2017 Office Action issued in Indian Patent Application No. 3334/DELNP/2009.
May 24, 2017 Office Action issued in European Patent Application No. 13771208.9.
May 15, 2017 Office Action issued in Japanese Patent Application No. 2015-533703.
Jan. 10, 2018 Office Action issued in Chinese Patent Application No. 201510612697.2.
Mar. 15, 2018 Office Action issued in U.S. Appl. No. 13/575,759.
Apr. 2, 2018 Examiner's Answer issued in U.S. Appl. No. 14/581,549.
Dec. 6, 2018 Office Action issued in U.S. Appl. No. 13/575,759.

* cited by examiner

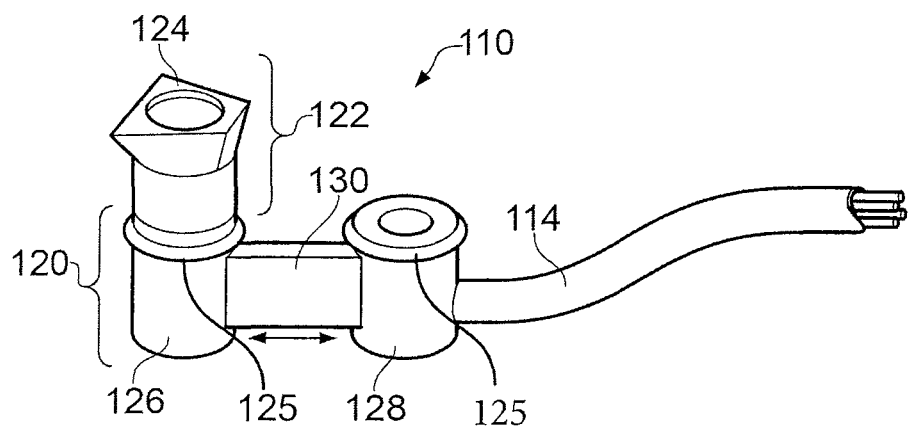
FIG. 4
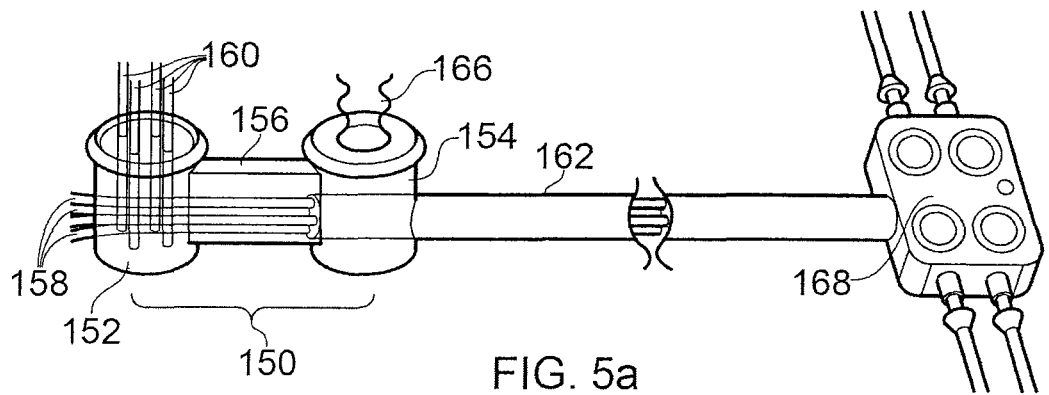
FIG. 5a
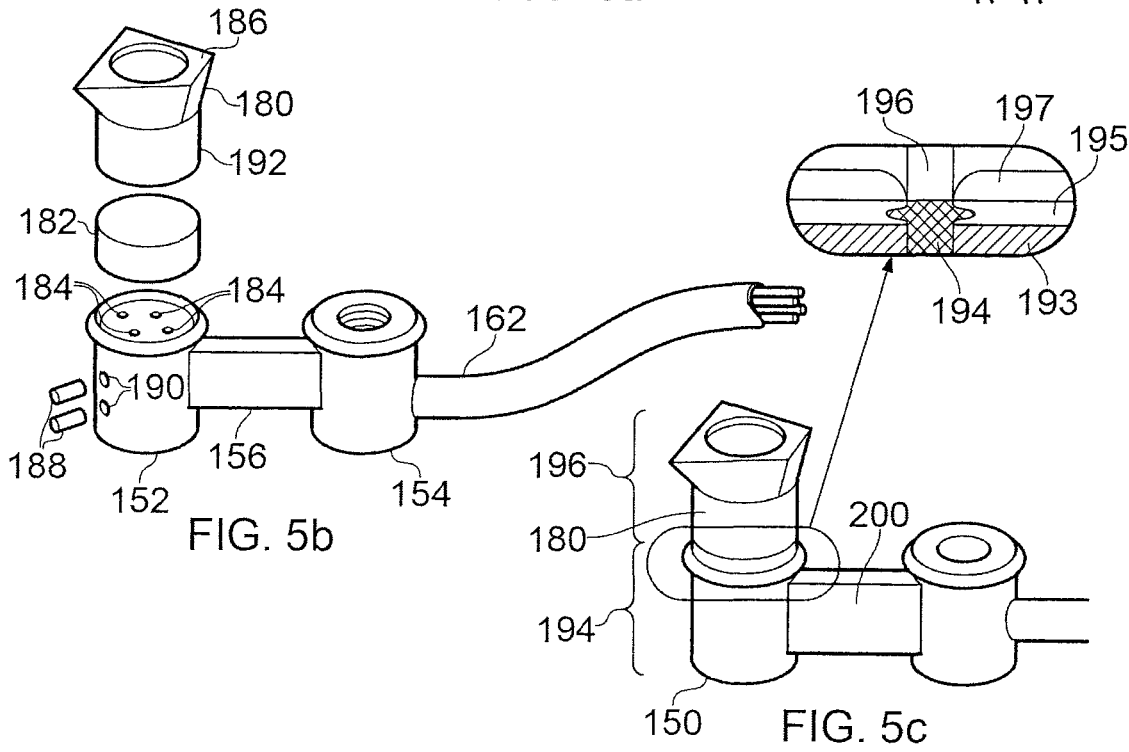
FIG. 5b
FIG. 5c (before)   (after)

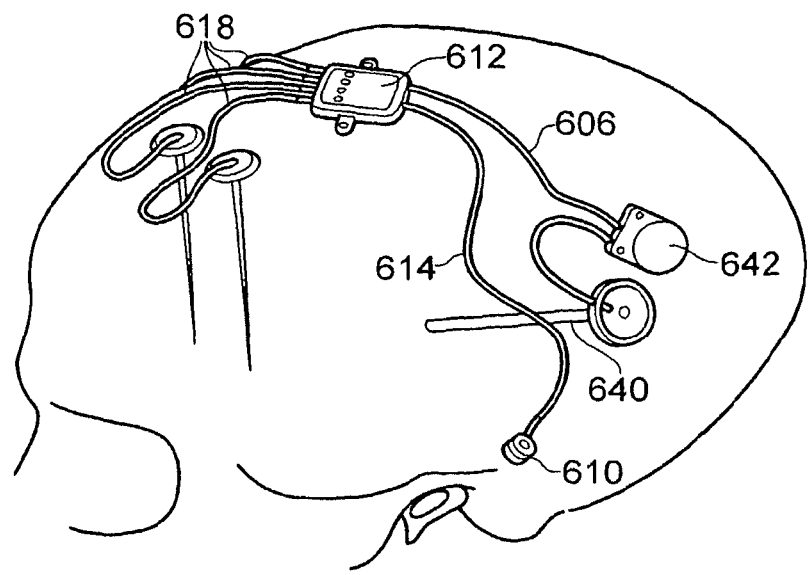
FIG. 15
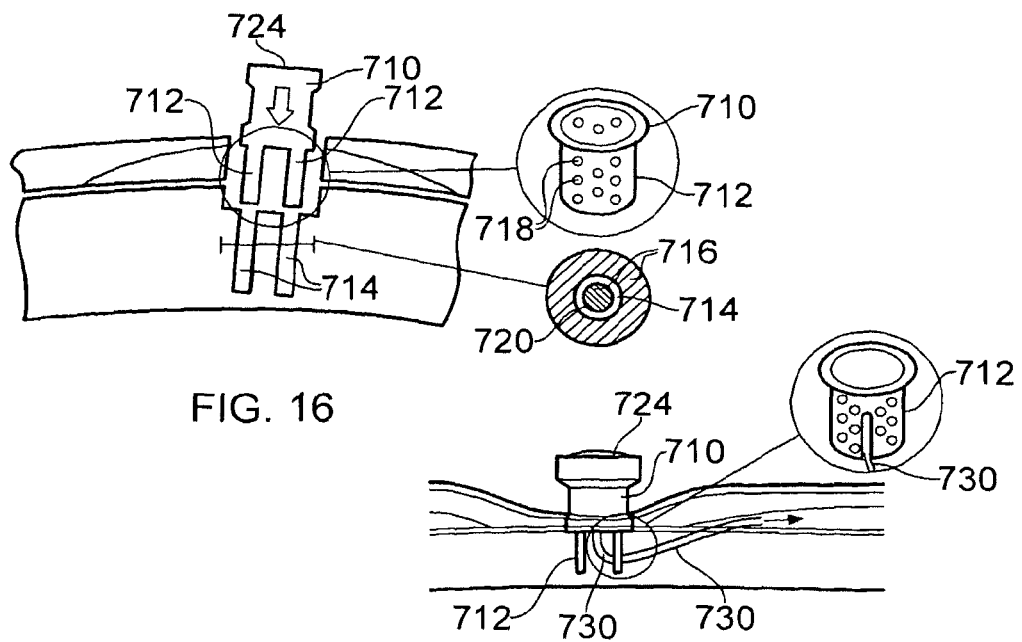
FIG. 16
FIG. 17

PERCUTANEOUS DRUG DELIVERY APPARATUS

This is a Continuation of application Ser. No. 13/575,769, filed Jul. 27, 2012, which is a National Stage of Application No. PCT/GB2011/000183, filed Feb. 11, 2011. The prior applications, including the specification, drawings and abstracts are incorporated herein by reference in their entirety.

BACKGROUND

The present invention relates to drug delivery apparatus and in particular to neurological drug delivery apparatus comprising a skull mountable percutaneous fluid delivery device.

Implantable drug delivery systems are known for the treatment of neurological conditions where the blood brain barrier prevents many systemically administered drugs from reaching the desired target, or where the delivery of drugs or therapeutic agents to targets other than the desired target may produce unacceptable side affects. In particular, it is known to deliver drugs and other therapeutic agents directly into the brain parenchyma via one or more implanted catheters. Examples of this type of therapy include the infusion of gamma-amino-butyric acid agonists into an epileptic focus or pathway that will block its transmission, the delivery of cytotoxic agents directly into a brain tumour, and the infusion of neurotrophic agents for the protection and repair of failing or damaged nerve cells. The infusion of such neurotrophic agents can be used to treat a variety of neurodegenerative disorders including Parkinson's disease, Alzheimer's disease and Amyotrophic Lateral Sclerosis, and may also be useful in stimulating the repair of damaged neural tissue after injury from trauma, stroke or inflammation.

Fully implantable neurological drug delivery systems have been used for many years. A pump is typically located in the abdomen and tubing is tunnelled subcutaneously to implanted intraparenchymal catheters. Examples of implantable drug delivery pumps for delivery of therapeutic agents to the brain parenchyma are shown, for example, in U.S. Pat. Nos. 4,013,074, 4,692,147, 5,752,930 and WO2004/105839.

It is also known to provide so-called percutaneous access devices that provide a fluid connection between the inside and the outside of the body. Examples of devices that can be used for providing external access to a subject's blood stream are described in US2004/0249361, U.S. Pat. Nos. 6,607,504 and 5,098,397. A stabilised percutaneous access device for neurological applications has also been described previously in WO2008/062173. Transcutaneous fluid transfer apparatus comprising a plate that can be fixed to the skull using bone screws is described in WO97/49438. A percutaneous transferring device that can be screwed to bone is also disclosed in WO99/34754.

SUMMARY

According to a first aspect of the present invention, an implantable percutaneous fluid delivery device is provided that comprises; a subcutaneous base portion comprising one or more ports for supplying fluid to one or more implanted catheter devices, and a percutaneous portion comprising an extracorporeal surface, the one or more ports of the subcutaneous base portion being accessible from the extracorporeal surface of the percutaneous portion, wherein the subcutaneous base portion is at least partially insertable into a complementary recess formed in a bone, the subcutaneous base portion comprising one or more features for gripping the internal surface of such a complementary recess thereby directly anchoring the subcutaneous base portion to the bone.

The present invention thus relates to an implantable percutaneous fluid delivery device or port unit for use in delivering fluid, such as therapeutic agents, to selected targets within the body. The implantable percutaneous fluid delivery device has one or more outlets or ports that are separately connectable to one or more implanted catheter devices. The implantable percutaneous fluid delivery device is particularly suited for use in delivering therapeutic agents to targets within the brain using one or more associated implanted intraparenchymal catheter devices.

The implantable percutaneous fluid delivery device comprises a subcutaneous base portion comprising one or more ports for supplying fluid to one or more implanted catheter devices. The term subcutaneous as used herein is intended to define a location below the outer surface of the skin. As described below, the subcutaneous base portion is preferably implantable below all of the skin A percutaneous portion is also provided as part of the device that extends from the subcutaneous base portion and comprises an extracorporeal surface. As would be understood by those skilled in the art, when implanted a percutaneous device crosses the skin to provide a connection between the inside and outside of the body. The one or more ports of the subcutaneous base portion are accessible from the extracorporeal surface of the percutaneous portion; in other words, the extracorporeal surface (i.e. a surface accessible from outside of the body) provides fluidic access to the one or more outlet ports of the subcutaneous base portion of the device. It should be noted that the subcutaneous base portion and percutaneous portion may be formed together or may be formed as separate components that are attached together before use.

The subcutaneous base portion of the device of the first aspect of the present invention is at least partially insertable into a complementary recess formed in a bone (e.g. a skull bone). The subcutaneous base portion also comprises one or more features for gripping the internal surface or wall(s) of such a recess thereby directly securing or anchoring the subcutaneous base portion to the bone. In this manner, a mechanical fit (e.g. a friction fit) of the device can be obtained immediately on implantation without the need for bone screws or the like. Over time, any mechanical stresses will dissipate as the bone grows or reforms. For longer term (e.g. chronic) applications, it is thus preferred that at least part of the subcutaneous base portion osseointegrates after implantation. As described in more detail below, it is thus preferred that some or all of the subcutaneous base portion integrates with bone after implantation thereby anchoring or securing the device in place for the longer term. Such a bone anchored device has the advantage that it can be more securely attached to a subject than a floating or skin stabilised port. Furthermore, there is no mechanical load placed on soft tissue when external fluid connectors are attached to the extracorporeal surface of the device. This reduces the possibility of skin tears or damage that may increase the risk of infection.

Advantageously, the subcutaneous base portion is shaped to provide a friction fit with a complementary recess formed in a bone. The base portion may, for example, have a rough surface and/or other surface features (e.g. ridges, protrusions etc) that engage and grip the recess formed in the bone. For example, the device may be secured in place by a push-fit or press-fit action. The device may be forced into tight engagement with the bone recess using an impactor or other tool. Providing a friction fit and optionally promoting osseointegration permits a simpler surgical implantation procedure and a more reliable attachment of the device to a subject than can be achieved using glue, screws or the like.

As mentioned above, it is preferred, but not essential, that at least part of the subcutaneous base portion osseointegrates. In other words, the bone conveniently integrates with (e.g. grows into, onto and/or through) the subcutaneous base portion after implantation. Preferably, the base portion comprises a rough surface that promotes osseointegration. The base portion may additionally or alternatively comprise a coating that promotes osseointegration. For example, a coating of plasma sprayed titanium and/or hydroxyapatite on the outer surface of the subcutaneous base portion may be provided. Promoting osseointegration in this manner has the advantage of preventing the subcutaneous base portion moving (e.g. slipping or twisting) or becoming detached from the bone after implantation. Promoting osseointegration is, however, superfluous when the device is used for short term (e.g. acute) surgical interventions.

When implanted, at least part (and preferably most) of the subcutaneous base portion is located below the outer surface of a bone. The device thus preferably includes a feature or features that allow the depth of insertion of the device into an appropriate recess formed in a bone to be predefined. Advantageously, the base portion comprises a protruding lip or step(s) for engaging the outer surface of a bone around the periphery of a recess formed in that bone. Such a lip thus sits on the outermost bone surface when inserted and, as well as setting the depth of insertion, also allows the device to be implanted in a hole that passes all the way through a bone.

Advantageously, the subcutaneous base portion comprises a first part that is attached or attachable to the percutaneous portion. Conveniently, an elongate section is provided that protrudes from the first part. Preferably, when the device is anchored to a bone the body, the whole of the elongate section is located within a recess or trench formed in that bone. This allows the elongate section to be completely implanted within the bone; the recess or trench containing the elongate section may also be backfilled with bone chippings to bury the elongate section. In this manner, the elongate portion lies below the outer surface of the bone when implanted. The elongate section may comprise a rigid, e.g. tubular, member. The elongate section may comprise a length of tubing that protrudes from the first part and terminates at a fluid connection to a supply tube. Alternatively, the elongate section may comprise the proximal end of a longer section of tubing; for example, an end of tubing that leads to a implantable fluid router or the like. Providing such a protruding elongate section (i.e. that can be buried in a bone recess) also helps prevent rotation of the device relative to the bone after implantation (e.g. when establishing fluid connections).

Advantageously, the subcutaneous base portion comprises a second part, the first and second parts of the subcutaneous base portion being connected by the elongate section. The first and second parts may be locatable in separate, spaced apart, recesses formed in the bone. A channel or trench between the first and second parts may also be formed in the bone for receiving the elongate section. The second (subcutaneous) part may include one or more filters (e.g. air and/or bacterial filters). The second part may also include one or more tube grips and/or tube connectors that enable one or more supply tubes and/or catheter devices to be operatively connected to the implantable percutaneous fluid delivery device. The second part may include skull fixation means, such as flanges, ribs or other fixtures, that allow it to be attached (e.g. push-fitted or screwed) to the bone. Securing both the first and second parts of the subcutaneous base portion directly to the bone has the advantage that the device can be more firmly anchored in place and is less likely to become detached with time and/or use.

The one or more fluid channels of the ports preferably extend through the elongate section. In this manner, the buried elongate section may separate the percutaneous portion from the part (e.g. the second part) of the subcutaneous base portion to which the supply tube(s) carrying fluid to the associated catheter devices are attached. Advantageously, the elongate section is at least 5 mm long. The elongate section is more preferably at least 10 mm long, more preferably at least 20 mm long and more preferably at least 30 mm long.

The elongate section has been found to act as a barrier to any infection present at the percutaneous portion (i.e. the location where infection is most likely to occur) from passing to the implanted catheter devices. In particular, the skin can be thinned in the region of the elongate section during implantation of the device to promote bio-integration of the dermis with the periosteum. This local bio-integration of the skin with the periosteum effectively provides a living seal between the bone and the skin that reduces the risk of infection present at the percutaneous portion from spreading along the elongate section. Providing such an elongate section has thus been found to provide an effective infection barrier that helps prevent any infection present at the device-skin interface from reaching catheter devices attached to the implantable percutaneous fluid delivery device.

The implantable percutaneous fluid delivery device may include a single port that provides fluidic access to a single catheter device. However, as the device is anchored directly to bone, it is particularly suited for use with a plurality of ports. In particular, the greater force required to establish a plurality of fluid connections (e.g. by forcing a plurality of needles through a septum) is passed directly to the bone and there is minimal mechanical load on the soft tissue that could cause tearing and thereby increase the risk of infection. Advantageously, the device comprises two or more ports. More preferably, the device may comprise at least three, at least four or more than four ports. Each port may be in fluid communication with a separate catheter device, optionally via an implantable router unit or other fluid routing device.

The device may comprise one or more components for filtering any fluid it receives. For example, the device may comprise a bacterial filter and/or a gas (e.g. air) filter or vent. The device may also include various seals, flow control components and tubes or tube grips etc.

Advantageously, the subcutaneous base portion comprises at least one subcutaneous fluid inlet. Each subcutaneous fluid inlet is preferably for receiving fluid from a remotely implanted pump (e.g. from a pump implanted in the abdomen). A subcutaneously tunnelled tube may be provided to supply fluid to the subcutaneous fluid inlet from the remotely implanted pump. Fluid received at the subcutaneous fluid inlet is preferably routable to the one or more ports. For example, the fluid received at the subcutaneous fluid inlet may be routed to each, or some, of the one or more ports.

The subcutaneous fluid inlet may receive the fluid under pressure (e.g. at a constant pressure). The device may include one or more flow rate controllers to control the flow rate of fluid from the subcutaneous fluid inlet to the one or more ports. The fluid received at the subcutaneous fluid inlet may be a non-therapeutic or carrier fluid; e.g. it may comprise buffered saline, artificial CSF or another suitable inert fluid.

The fluid pumped to the subcutaneous fluid inlet may be from a reservoir (e.g. a reservoir provided as part of, or separately from, the pump) or collected from the body cavity. For example, the fluid may comprise CSF collected using an implanted intracranial shunt for neurological applications. Providing such a subcutaneous fluid inlet allows a constant flow of fluid (e.g. at a low flow rate of around 0.2 ml per hour) to the implanted catheter device. This is especially advantageous for neurological applications that use implanted catheters devices having a small internal diameter of, say, less than 0.25 mm; the constant fluid flow has the advantage of preventing such catheters becoming blocked during use.

The subcutaneous fluid inlet may be in permanent fluid communication with the one or more ports. Advantageously, accessing the one or more ports via the extracorporeal surface substantially blocks the flow of fluid to the one or more ports from the subcutaneous fluid inlet. In other words, accessing the ports via the extracorporeal surface (e.g. to deliver a therapeutic agent via the implanted catheter devices) may reduce or obstruct the fluid flow from the subcutaneous inlet to the one or more ports. The device may include one or more valves that block the fluid flow when the ports are accessed from the extracorporeal surface. The extracorporeal surface thus allows the flow of carrier fluid to be stopped or bypassed whilst the therapeutic agent is delivered.

The percutaneous portion of the device, and in particular the interface between the skin and the device, is the most likely site where infection may occur. It is thus preferred that at least some of the percutaneous portion comprises a peripheral surface that encourages tissue (skin) ingrowth. For example, a lower region of the peripheral surface of the percutaneous portion may be porous or roughened. This may be achieved by making at least part of the percutaneous portion from a porous material such as porous titanium, by coating it with a porous/rough material (e.g. hydroxyapatite or a nano fibrous matrix) or by texturing the surface.

Preferably, the surface of the percutaneous portion is rough where, when implanted, it contacts the dermis. This helps to reduce the ingress of bacteria or other microbes by encouraging the dermis to form a tight junction with the surface of the percutaneous portion. Furthermore, as the mechanical load imparted on the device is transmitted directly to the bone, accessing the ports via the extracorporeal surface does not load or disturb this tissue interface thereby also reducing the chances of infection. Preferably, at least some of the percutaneous portion comprises a smooth peripheral surface. For example, an upper region of the peripheral surface of the percutaneous portion may be smooth (e.g. coated with a diamond like coating). Preferably, the surface of the percutaneous portion is smooth where, when implanted, it lies adjacent the epidermis. The smooth surface inhibits tissue in-growth and can be kept clean thereby further reducing the risk of infection of the underlying dermis.

As described above the one or more ports of the device are accessible from the extracorporeal surface of the percutaneous portion. The device preferably comprises a seal to prevent or reduce the ingress of microbes. Any appropriate seal may be used. Conveniently, the seal is in the form of a bung, made from, for example, rubber or silicone. Advantageously, the seal comprises an antimicrobial (e.g. antibacterial) material; e.g. the rubber or silicon bung may be silver impregnated. The extracorporeal surface of the device is preferably arranged to allow access to the one or more ports through or via the seal. For example, the extracorporeal surface may be provided with one or more apertures or may be removable. In use, a therapeutic agent may be introduced to the port by, for example passing a needle through the aperture and through the bung and injecting the agent into the port. The seal may be replaceable (e.g. under appropriate sterile conditions) from the extracorporeal side of the device.

The above described device may be used for delivering therapeutic agent(s) to the central nervous system (e.g. to the brain or spinal cord). Advantageously, the above described device is used for delivering therapeutic agent(s) to the brain. The present invention may thus comprise neurological apparatus comprising a percutaneous fluid delivery device as described above. The apparatus may also comprise one or more intraparenchymal catheter devices that can be implanted to deliver fluid to one or more target sites within the brain parenchyma.

Advantageously, the percutaneous fluid delivery device is connected to the one or more intraparenchymal catheter devices via an implantable router unit. The implantable router unit may have one or more inlets for routing fluid received from the percutaneous fluid delivery device to one or more outlets that are connected to the one or more catheter devices. The apparatus conveniently comprises a supply tube having one or more lumens. Preferably, the supply tube is at least 5 cm long, more preferably at least 10 cm long and more preferably at least 15 cm long. Providing such a length of supply tube acts to separate the router unit from the percutaneous fluid delivery device thereby reducing the risk of infection reaching the router unit from the percutaneous fluid delivery device. The one or more ports of the percutaneous fluid delivery device may be connected to the one or more inlets of the router unit via the supply tube. Preferably, the percutaneous fluid delivery device comprises a plurality of ports connected to a plurality of catheter devices via a multi-lumen supply tube and an implantable router unit having a plurality of inlets that are each separately connected to one of plurality of outlets.

Advantageously, the implantable router unit comprises one or more fluid filtration components. For example, the implantable router unit may comprise a gas (e.g. air) filter or vent and/or a bacterial filter. If the implantable router unit has a plurality of separate fluid paths therethrough (e.g. if it comprises a plurality of inlets that are each connected to one of a plurality of outlets) it is preferred that separate filtration is applied to each fluid path. Providing filtration as part of the implantable router unit has the advantage that the filtration occurs in close proximity to the catheter devices. The length of the path from the filter to the point of fluid delivery is thus minimised thereby minimising the introduction of contaminants or air into the fluid during its transmit through the fluid delivery apparatus.

Advantageously, the apparatus comprises an external (to the body) fluid connector unit for cooperating with the extracorporeal surface of the percutaneous fluid delivery device to provide fluid communication with the ports. The extracorporeal surface and the external fluid connector unit may be configured to mate to provide the required fluidic link(s) with the one or more ports. As mentioned above, the extracorporeal surface may provide access to a plurality of ports. The external fluid connector unit may then comprise, for example, a plurality of needles that penetrate a septum of the percutaneous fluid delivery device to provide separate fluidic access to each of the ports. Preferably, if the extracorporeal surface provides access to a plurality of ports, one or more alignment features are provided to ensure the fluid connector unit is attachable to the extracorporeal surface in only a single, unique, orientation. The alignment feature may comprise the shape of the mating parts of the extracorporeal surface and the external fluid connector unit and/or alignment prongs and/or any other suitable physical features. The provision of such alignment features ensures that the fluid lines of the fluid connector unit are always placed in fluid communication with the same ports of the percutaneous fluid delivery device. A suitable fluid connector is described in WO2007/104961.

A locking mechanism may be provided to lock the fluid connector unit to the extracorporeal surface of the percutaneous fluid delivery device. This may be used to prevent unwanted or uncontrolled detachment of the fluid connector unit from the percutaneous fluid delivery device. The external fluid connector unit may be connected to external pump(s) or to syringes or other means of pumping therapeutic agent through the apparatus. The external fluid connector unit may also include in-line filters. The invention also extends to a separate fluid connector unit for cooperating with the extracorporeal surface of a percutaneous fluid delivery device of the type described above in order to provide fluid communication with the one or more ports of said device.

The percutaneous fluid delivery device may also comprise a protective cap. The protective cap may be arranged to releasably engage the extracorporeal surface of the percutaneous fluid delivery device. When attached, the cap may prevent access to the ports of the device. If the percutaneous fluid delivery device comprises a septum seal, the cap preferably protects the septum seal. A locking mechanism may be provided to lock the protective cap to the extracorporeal surface of the percutaneous fluid delivery device. This locking mechanism may be used to prevent unauthorised or unwanted detachment of the protective cap from the percutaneous fluid delivery device (e.g. by a patient). The present invention also extends to a protective cap for a percutaneous fluid delivery device as described above. Warnings or other indications may be marked on the cap. The cap or percutaneous fluid delivery device may include an electronic tag that stores information on the implanted fluid delivery device and/or treatment information.

In addition to providing a percutaneous fluid delivery device having one or more ports through which fluid can be routed, one or more further connector functions may be provided. For example, the device may provide one or more electrical connections and/or one or more optical connections. Advantageously, the one or more ports of the device may themselves be used to transmit electricity, light or ultrasound energy via the fluid medium.

According to a further aspect of the invention, a jig is provided for implanting a percutaneous fluid delivery device as described above. The jig preferably provides a template for cutting a recess in bone (e.g. in a skull bone) into which the subcutaneous base portion of the percutaneous fluid delivery device can be friction fitted. The jig may include temporary attachment means (e.g. an aperture for receiving bone screws) that allow it to be secured to bone whilst the appropriate recess is formed. A drill or other bone cutting device may be provided to form the recess in the bone using the jig as the template. The present invention, in a yet further aspect, also relates to a surgical method of implanting a percutaneous fluid delivery device of the type described above. Preferably, such a surgical procedure employs the above described jig. For neurological applications, the percutaneous fluid delivery device is preferably implanted in the skull adjacent the ear. The method may also include locally thinning the scalp in the region where the device is implanted.

According to a further aspect of the invention, an implantable percutaneous fluid delivery device is provided that comprises a subcutaneous base portion comprising one or more ports for supplying fluid to one or more implanted catheter devices, and a percutaneous portion comprising an extracorporeal surface, the one or more ports of the subcutaneous base portion being accessible from the extracorporeal surface, the subcutaneous base portion comprising a first part that is attached to the percutaneous portion and an elongate section that protrudes from the first part, wherein, when the device is implanted in the body, at least part of the elongate section is located (e.g. buried) within a recess formed in the bone. Preferably, the subcutaneous base portion further comprises a second part, the first part being connected to the second part by the elongate section. Conveniently, when the device is anchored to a bone the body, the whole of the elongate section is located within a recess or trench formed in that bone. Each of the one or more ports preferably comprises a fluid channel that extends from the first part to the second part though the elongate section. The device may also include any one or more of the other features that are described herein.

According to a further aspect of the invention, an implantable percutaneous fluid delivery device is provided that comprises a subcutaneous base portion comprising one or more ports for supplying fluid to one or more implanted catheter devices and a percutaneous portion comprising an extracorporeal surface, the one or more ports of the subcutaneous base portion being accessible from the extracorporeal surface of the percutaneous portion, wherein the subcutaneous base portion is at least partially insertable into a complementary recess formed in a bone and at least part of the subcutaneous base portion osseointegrates following implantation. Preferably, the subcutaneous base portion comprises at least one of a rough surface and a coating that promotes osseointegration. The device may also include any one or more of the other features that are described herein.

An implantable router unit is also described herein that comprises one or more inlets and one or more outlets, wherein fluid is routable from the one or more inlets to the one or more outlets. The router unit may comprise an air filter for removing air from fluid routed from the one or more inlets to the one or more outlets. The implantable router unit may include a bacterial filter. Preferably, the implantable router unit comprises a plurality of inlets that are each separately connected to one of the plurality of outlets. If the implantable router unit has a plurality of separate fluid paths therethrough (e.g. if it comprises a plurality of inlets that are each connected to one of a plurality of outlets) it is preferred that separate air filtration is applied to each fluid path. For example, each fluid path may include a separate filter chamber. Conveniently, the filter (e.g. each filter chamber) comprises an hydrophobic layer and a hydrophilic layer to provide a gas (e.g. air) venting or filtering function. In other words, the filter separates and removes any gas (e.g. air) from the liquid therapeutic agent being delivered. A membrane or diaphragm may also be provided (e.g. adjacent the hydrophobic layer) through which any vented air dissipates into the body cavity. The implantable router unit may be provided as part of a catheter device. For example, an implantable router unit having a single inlet and single outlet may be incorporated in the head of an intra-parenchymal catheter.

An implantable percutaneous fluid delivery device is also described herein that comprises; a subcutaneous base portion comprising one or more ports for supplying fluid to one or more implanted catheter devices, and a percutaneous portion extending from the subcutaneous base portion, wherein the percutaneous portion comprises an extracorporeal surface and the one or more ports of the subcutaneous base portion are accessible from the extracorporeal surface. The subcutaneous base portion may comprise a subcutaneous fluid inlet for receiving fluid from a remotely implanted pump, wherein fluid received at the subcutaneous fluid inlet is routable to the one or more ports. Advantageously, accessing the one or more ports via the extracorporeal surface substantially blocks the flow of fluid to the one or more ports from the subcutaneous fluid inlet. The subcutaneous base portion may also be anchored to the bone of a subject and at least part of the subcutaneous base portion may promote osseointegration. The device may also include any of the other features that are described herein.

An implantable percutaneous fluid delivery device is also described herein that comprises a subcutaneous base portion comprising one or more ports for supplying fluid to one or more implanted catheter devices, and a percutaneous portion extending from the subcutaneous base portion, wherein the percutaneous portion comprises an extracorporeal surface and the one or more ports of the subcutaneous base portion are accessible from the extracorporeal surface, the subcutaneous base portion comprising a first part that is attachable to the percutaneous portion and an elongate section that protrudes from the first part, the fluid channels defined by the ports extending through the elongate section, wherein, when the device is implanted in the body, the whole of the elongate section is located within a recess formed in the bone.

An implantable percutaneous access device is also described herein that comprises; a subcutaneous base portion comprising one or more connections to one or more implanted devices, and a percutaneous portion extending from the subcutaneous base portion, wherein the percutaneous portion comprises an extracorporeal surface and the one or more connections of the subcutaneous base portion are accessible from the extracorporeal surface. The subcutaneous base portion is preferably directly anchorable to a bone of a subject and is configured to promote osseointegration after implantation. The one or more connections provided by the device may comprise at least one of an optical, electrical or fluidic connection. Advantageously, the subcutaneous base portion comprises a plurality of connections to a plurality of implanted devices.

An implantable percutaneous fluid delivery device is thus described herein. The device may comprise a subcutaneous base portion. The subcutaneous base portion may comprise one or more ports for supplying fluid to one or more implanted catheter devices. A percutaneous portion may be provided. The percutaneous portion may extend from the subcutaneous base portion. The percutaneous portion may comprise an extracorporeal surface. The one or more ports of the subcutaneous base portion are preferably accessible from the extracorporeal surface. The subcutaneous base portion is advantageously directly anchorable to a bone of a subject. The device may include any one or more of the other features that are described herein.

BRIEF DESCRIPTION OF THE DRAWINGS

The invention will now be described, by way of example only, with reference to the accompanying drawings in which;

FIGS. 5*a*-5*c* show one method for fabricating the percutaneous drug delivery port of the apparatus of FIG. 1, FIG. 15 shows a further implantable neurological drug delivery apparatus of the present invention having a CSF pump, FIG. 16 illustrates a bone mounting technique for securing a percutaneous drug delivery port to the skull, FIG. 17 shows the device of FIG. 16 when implanted in a skull.

DETAILED DESCRIPTION OF EMBODIMENTS

Figure 1:
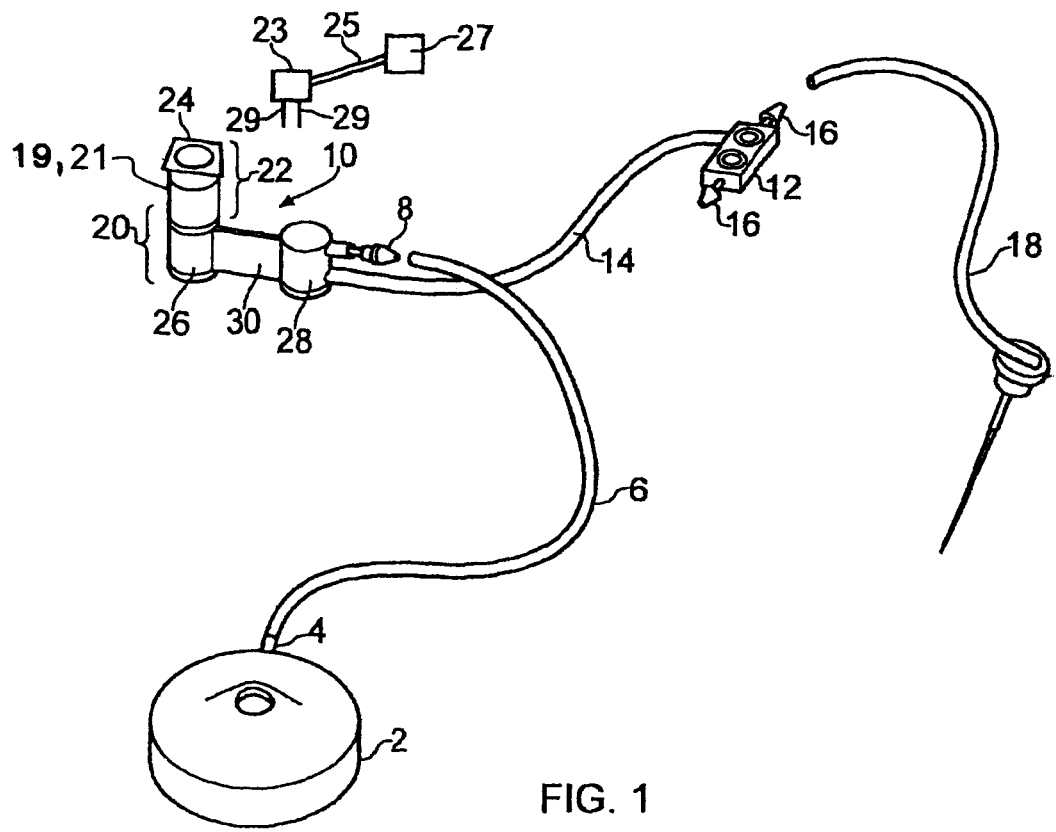
FIG. 1 shows implantable neurological drug delivery apparatus of the present invention.

Referring to FIG. 1, implantable neurological drug delivery apparatus of the present invention is shown. The apparatus comprises a constant pressure pump 2 that includes an internal reservoir and has an outlet 4 connected to the first end of a single lumen supply tube 6. Although a constant pressure pump 2 is shown, it should be noted that any implantable pump (e.g. a constant or programmable flow rate pump) can be employed. The second end of the supply tube 6 is connectable to the inlet 8 of a port unit 10. The port unit 10 comprises two outlets that are linked to the two inlets of a router unit 12 by a dual-lumen supply tube 14. The router unit 12 comprises two outlets 16, each in fluid communication with a respective lumen of the supply tube 14, that are each connectable to a neurological catheter device 18.

The port unit 10 comprises a subcutaneous portion 20 and a percutaneous portion 22 that has an extracorporeal surface 24. The subcutaneous portion 20 is suitable for at least partial insertion into an appropriately shaped recess formed in the skull. In particular, the subcutaneous portion 20 is coated with a material that promotes biointegration with bone after implantation and will thus become secured to the skull without the need for bone screws or the like. In other words, the subcutaneous portion 20 is osseointegrating (also termed osteointegrating). In this example, the coating or surface finish 21 provided on the external surface of the subcutaneous portion 20 comprises plasma sprayed titanium combined with hydroxy-apatite. Other coatings or surface finishes may be provided to produce a similar effect. There may also be provided on the external surface of the subcutaneous portion 20 a rough surface 19 for securing the subcutaneous portion 20 to the skull.

The subcutaneous portion 20 may be formed as a single component but comprises three discrete functional parts. In particular, a first substantially cylindrical part 26 of the subcutaneous portion 20 is connected to a second substantially cylindrical part 28 by an elongate joining section 30. As will be described in more detail below with reference to FIG. 3, the second substantially cylindrical part 28 has an inlet 8 for receiving carrier fluid from the pump outlet 4 and an exit for a dual-lumen supply tube 14 that comprise a separate lumen for supplying fluid to each of the two catheters 18 via the router unit 12. The first substantially cylindrical part 26 is also attachable to the percutaneous portion 22 thereby allowing external access to the separate fluidic pathways to the two catheter devices 18. In particular, the extracorporeal surface 24 comprises two sealed access ports that permit fluid (e.g. a drug or other therapeutic agent) to be injected into the fluid stream that runs from the pump 2 to the catheter devices 18.

An external fluid connector unit 23 is also provided that is releasably attachable to the extracorporeal surface 24 of the percutaneous portion 22. When the connector unit 23 is attached or mated with the port unit 10, a pair of protruding needles 29 penetrate the seal and thereby provide separate fluidic access to the two ports of the port unit 10. The needles of the fluid connector unit 23 may be separately connected to different channels of an external drug pump 27 or individual pumps via a multi-lumen tube 25. In this manner, the fluid connector unit 23 provides separate fluidic access to the different ports of the port unit 10 to enable the delivery of therapeutic agents or the like to the catheter devices 18. The fluid connector unit 23 may be attachable to the extracorporeal surface 24 in only one orientation to ensure the same needle always accesses the same port. A locking mechanism may also be provided to lock the fluid connector unit 23 to the extracorporeal surface 24 as and when required.

The first substantially cylindrical part 26 is connected to the second substantially cylindrical part 28 by the elongate joining section 30. The elongate joining section 30 comprises multiple lumens (in this case three) that provide the necessary fluidic pathways between the first and second substantially cylindrical parts 26 and 28. In addition, the provision of such an elongate joining section 30 has the benefit of reducing the infection risk. Infection risk is further reduced by spacing the port unit 10 apart from the router unit 12. This is described in more detail below.

Figure 2:
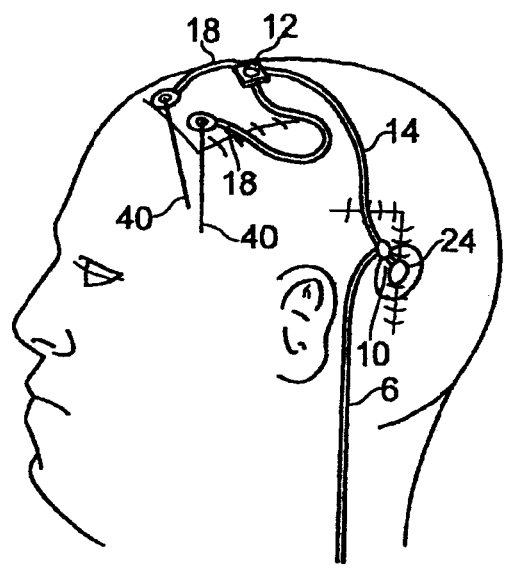
FIG. 2 illustrates the device of FIG. 1 implanted in a subject.

Referring to FIG. 2, the drug delivery apparatus described with reference to FIG. 1 is illustrated when implanted in the body. The constant pressure pump 2, which may comprise a diaphragm pump of known type, is not shown in FIG. 2 but is implanted in the abdomen. The supply tube 6 running from the pump 2 is tunnelled under the skin to the head of the subject. The port unit 10 is affixed within an appropriately dimensioned recess formed in the bone of the skull adjacent the ear; a technique for attaching the port unit to the skull is described in more detail below with reference to FIGS. 6 and 7a-7g. The supply tube 6 is connected to the inlet 8 of the port unit 10 and the dual-lumen supply tube 14 exiting the port unit 10 is subcutaneously tunnelled under the scalp to the router unit 12. The router unit 12 is secured to the skull, for example using bone screws, in the vicinity of the point where the catheter devices 18 pass through holes in the skull and enter the brain parenchyma.

The constant pressure pump 2 contains a reservoir that stores a carrier fluid, such as saline (e.g. buffered saline) or artificial cerebrospinal fluid (CSF). The pump 2 may be refillable in a known manner by percutaneous injection into a refill port provided on a surface of the pump 2. After implantation, the pump 2 supplies carrier fluid under pressure to the port unit 10 via the supply tube 6. The port unit 10 is arranged to continuously direct a small flow of carrier fluid to each of the catheter devices 18 via the dual-lumen supply tube 14 and router unit 12. The distal end 40 of each catheter device 18 is accurately positioned within the brain parenchyma at a required target site. Examples of suitable catheter devices are described in WO03/077785. Techniques for locating the catheters adjacent the required target sites in the brain are described in U.S. Pat. No. 6,609,020 and WO03/077784. The contents of these documents are hereby incorporated by reference.

For the majority of the time after implantation, the drug delivery apparatus is arranged to pump small volumes of carrier fluid into the brain parenchyma via the catheter devices 18. The constant, or substantially constant, flow of carrier fluid reduces the chance of the catheter devices 18 becoming occluded due to tissue in-growth. This allows the chronic implantation of catheter devices that include fine tubes having an outer diameter of less than 0.25 mm. When the delivery of therapeutic agents is required, the extracorporeal surface 24 of the percutaneous portion 22 of the port unit 10 provides separate access to the fluidic pathways to each catheter device 18 and thus permits the required dosage of therapeutic agent to be delivered to the target site(s). Such delivery of therapeutic agent may be performed continuously (e.g. over a period of a few hours or days) through each catheter in parallel. Alternatively, the delivery of therapeutic agent may be performed serially (e.g. through each catheter in turn) to minimise any side effects associated with the delivered agent.

For many years, fully implantable drug delivery systems have been preferred for neurological applications to minimise the chances of an infection bypassing the blood-brain barrier and entering the brain parenchyma at the point the barrier is penetrated by a catheter. Such fully implantable system have however been found to have a number of disadvantages; for example, the storage capacity can be limited and problems often arise delivering drugs that have a short shelf-life or need to be stored in a certain environment (e.g. at a certain temperature). The use of a single implanted pump also does not provide the flow control that is needed when delivering fluid in precise volumes to different site using multiple catheters. It can also be difficult to access a refill port of a subcutaneously implanted pump, especially in obese patients, and any subcutaneous leakage of therapeutic agent can provoke an immune response to such agents. Although percutaneous access ports or refill ports have been proposed previously, such ports tend to be implantable in the torso, thereby requiring long lengths of supply tubing that increase the dead volume of the system. This additional dead volume can reduce the control over drug delivery thereby reducing treatment efficacy in certain circumstances.

The drug delivery apparatus illustrated in FIGS. 1 and 2 includes a port unit 10 that attached to the skull, but the apparatus is configured such that the inclusion of the percutaneous portion 22 does not introduce an unacceptable increase in the risk of an infection bypassing the blood-brain barrier. A number of features of the apparatus minimise this infection risk and, as described below, some or all of such features may be included in the apparatus as required.

The subcutaneous portion 20 of the port unit 10 comprises a first substantially cylindrical part 26 that is connected to the second substantially cylindrical part 28 by the elongate joining section 30. As explained below, the majority of the subcutaneous portion 20 is located in a recess formed in the skull bone. In particular, the majority of the elongate joining section 30 is buried within the slot or recess formed in the skull. Preferably, the elongate joining section 30 is sub-flush to the outer surface of the skull bone and bone chipping or the like are placed on top of the elongate joining section 30 after implantation. This allows bone to regrow over the top of the elongate joining section 30 after implantation. After such bone growth, the first substantially cylindrical part 26 is separated from the second substantially cylindrical part 28 by a region that is buried within the skull bone. This acts as a infection barrier between the supply tube connections and the percutaneous part of the port unit 10 where infection is most likely to occur. In other words, the arrangement reduces the chance of any infection that arises at the interface between the skin and the protruding percutaneous portion 22 from passing to the supply tube 14 and migrating along the outer surfaces of the various tubes that lead to the catheter devices that bypass the blood-brain barrier. Furthermore, the size of the percutaneous part of the port unit 10 is minimised thereby reducing the size of incision required thereby further reducing the infection risk.

In addition, it can be seen that the router unit 12 is located away from the port unit 10. In this example, the router unit 12 is separated from the port unit 10 by about 15 cm of dual-lumen tubing 14. As noted above the most likely infection site is the interface between the skin and the percutaneous portion 22 of the port unit 10. Providing the router unit 12 between the tubing from the port unit 10 and the catheter devices 18 thus introduces a further barrier to infection.

Bacterial filters may be provided within the apparatus to remove any bacteria present in the carrier fluid or in the therapeutic agent that is delivered. A bacterial filter may, for example, be located in the port unit 10 (e.g. in the second substantially cylindrical part 28) and/or in the router unit 12. The pump 2 may also or alternatively include a bacterial filter. The apparatus may also comprise an air filter to remove any air bubbles present in the fluid delivered to the brain. Such air bubbles are most likely to arise at connections between tubes or at the point of infusion of therapeutic agent into the port unit 10. In this example, the air filter is placed in the router unit 12 so that it as close as possible to the catheter devices 18 thereby removing as much air from the apparatus as possible. Alternatively, or additionally, air filters may be provided in the port unit 10, for example in the second substantially cylindrical part 28.

Figure 3A:
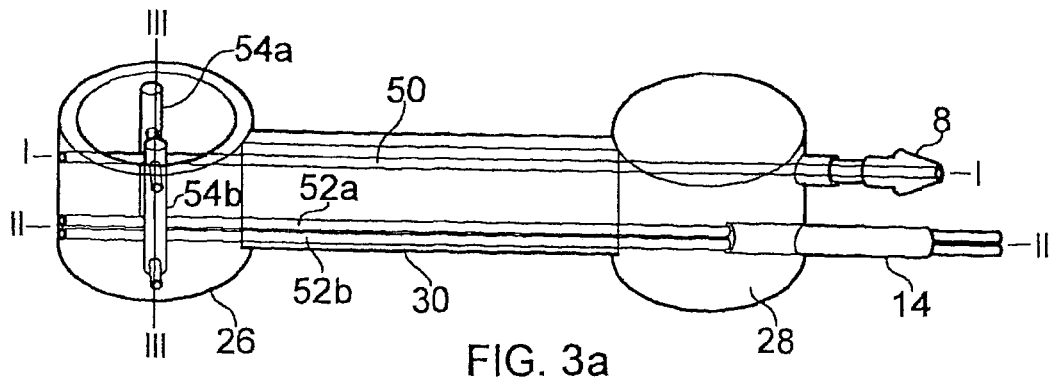
FIGS. 3*a*-3*d* shows various sections through the percutaneous drug delivery port of the apparatus of FIG. 1, FIG. 4 show the percutaneous drug delivery port of the apparatus of FIG. 1 when assembled.
Figure 3B:
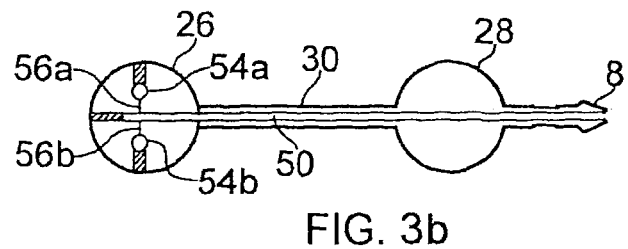
Figure 3C:
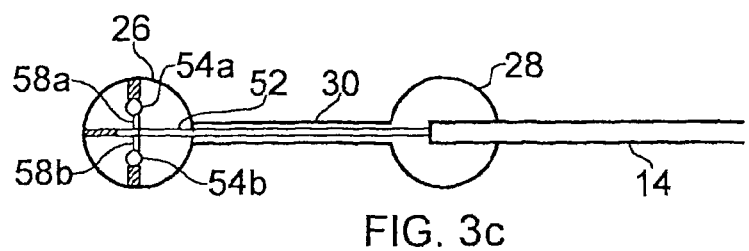
Figure 3D:
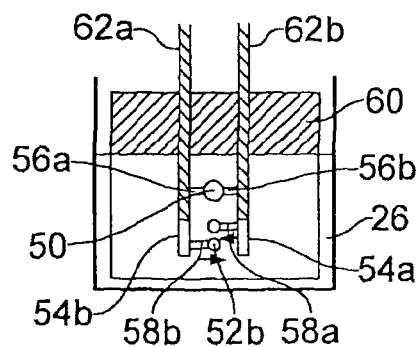

Referring to FIGS. 3a-3d, the internal configuration of the subcutaneous portion 20 of the port unit 10 is shown. In particular, FIGS. 3b, 3c and 3d are sections through the planes I-I, II-II and III-III respectively that are shown in FIG. 3a. As outlined above, the subcutaneous portion 20 of the port unit 10 comprises a first substantially cylindrical part 26 that is connected to a second substantially cylindrical part 28 by an elongate joining section 30.

The inlet 8 provided on the second part 28, which receives fluid under pressure from the remotely located pump, is in fluid communication with an inflow conduit 50 that passes through the elongate joining section 30 to the first part 26. Two outflow conduits 52a and 52b are also routed from the first part 26 back to the second part 28 via the elongate joining section 30. The outflow conduits 52a and 52b are in fluid communication with lumens of the dual-lumen supply tube 14. The first part 26 also comprises two vertical channels 54a and 54b. The inflow conduit 50 is in fluid communication with each of the vertical channels 54a and 54b via flow restricting channels 56a and 56b. Linking channels 58a and 58b provide fluid communication between the vertical channels 54a and 54b and the respective outflow conduits 52a and 52b.

The two vertical channels 54a and 54b are sealed at one end by a rubber bung 60 which may be provided as part of the percutaneous portion 22 of the port unit 10; the rubber bung 60 is shown in FIG. 3d. The rubber bung 60 permits fluid delivery needles 62a and 62b to enter the vertical channels 54a and 54b respectively. When a fluid delivery needle is inserted into its associated vertical channel, the flow of carrier fluid into that vertical channel is substantially blocked. Instead, fluid expelled from the needle tip passes through the associated linking channel and outflow conduit to the attached catheter device. It should be noted that such an arrangement permits the type, amount and flow rate of the therapeutic agent delivered via each catheter device to be separately controlled. In the absence of an inserted fluid deliver needle, the flow restricting channels 56a and 56b dispense carrier fluid into the respective vertical channels. The flow restricting channels 56a and 56b also perform the function of providing separate flow control over the amount of carrier fluid that passes to each catheter device. Although needle/septum based fluid connections are described above, it should be noted that needleless fluid connections could alternatively be provided.

It should be noted that although the above described example illustrates a port unit suitable for delivering fluid to two catheter devices, similar port units may be fabricated for use with fewer or more catheter devices. Furthermore, although continuous flush through of a carrier fluid is advantageous in certain applications (for example when using very fine catheters that may otherwise become occluded) it is not essential. A port unit similar to that described above but without the inlet for the carrier fluid could thus be provided.

Referring to FIG. 4, a port unit 110 is illustrated for use without a continuous supply of carrier fluid. The port 110 comprises a subcutaneous portion 120 and a percutaneous portion 122 that has an extracorporeal surface 124. The subcutaneous portion 120 comprises a first substantially cylindrical part 126 that is connected to a second substantially cylindrical part 128 by the elongate joining section 130. The proximal end of a four lumen supply tube 114 protrudes from the second part 128. The distal end of the four lumen supply tube 114 may terminate at a router unit (not shown) to which four separate catheter devices (not shown) are connected. Lips 125 for engaging the surface of the bone around a recess formed in the bone are also provided.

The first substantially cylindrical part 126 comprises four vertical internal channels that are in separate fluid with four conduits that pass from the first part 126 to the second part 128 through the elongate joining section 130. The four conduits are in separate fluid communication with respective lumen of the four lumen supply tube 114. The percutaneous portion 122 of the port unit 110 comprises a rubber bung (not shown) that seals one end of the vertical channel. A fluid delivery needle may be inserted through the rubber bung into any one or more of the vertical channels thereby permitting fluid to be pumped along each conduit to the associated catheter device. In this manner, fluid may be supplied to the required catheter device or devices as and when required.

It can thus be seen that the port unit 110 is similar to the port unit 10 described with reference to FIGS. 1 to 3, but does not comprise an inlet for providing the continuous supply of carrier fluid from an abdominal pump. Apparatus comprising the port 110 may be used with catheters having a sufficiently large diameter to prevent occlusion or if acute or short term infusion is required.

Referring to FIGS. 5a-5c, a method will be described for moulding a port unit such as that shown in FIG. 4 from a plastic material, such as PEEK.

FIG. 5a shows a moulded plastic subcutaneous portion 150 of the port unit that comprises a first part 152, a second part 154 and a elongate section 156 that joins the first and second parts. During the moulding process, four wires 158 extend through the subcutaneous portion 150 to form four fluid conduits. Four needles 160, which each intersect one of the wires 158, provide the vertical channels. After moulding, the wires 158 and needles 160 are withdrawn to form the required conduits and channels respectively. An overmoulded or sheathed four lumen supply tube 162 can then be attached to the second part 154 of the port unit. The outer sheath of the supply tube 162 is secured in place by a locking screw 166. Prior to securing the sheath in place, a fluidic connection is provided between each lumen of the supply tube 162 and one of the conduits within the port. As described above, the distal end of the supply tube 162 may be connected to a router unit 168

As shown in FIG. 5b, a percutaneous portion 180 may then be attached, for example using laser welding, to the surface of the first part 152 of the subcutaneous portion 150. The end of the conduits 190 formed during moulding are also sealed using plugs 188. The percutaneous portion 180 includes a rubber bung 182 that seals the ends of the four vertical channels 184 formed in the first part 152 of the subcutaneous portion 150. The percutaneous portion 180 also comprises an extracorporeal surface 186 having four access holes that each allow a needle to be passed through the rubber bung 182 into an associated one of the vertical channels 184.

FIG. 5c shows the port unit after the step of plasma spraying a layer of titanium 200 onto the lower part 194 of the port unit. This plasma spraying step may be followed by a step of applying a layer of hydroxy-apatite. It should be noted that the upper part 196 of the percutaneous portion 180 is masked during this procedure and is therefore not coated with the titanium or hydroxy-apatite. This upper part 196 may comprise a diamond like coating (DLC) 192 that provides a smooth surface or it can be made from a smooth material such as titanium.

As explained above the subcutaneous portion 150 osseointegrates with the skull bone 193 into which it is embedded; this is shown in the inset to FIG. 5c. As also shown in the inset to FIG. 5c, the lower part 194 of the port unit extends so that the dermis 195 (which may also be thinned to provide an improved interface between the dermis and the periosteum) grows into or bio-integrates with its roughened surface. The epidermis 197 of the skin is arranged to lie adjacent the smooth surface of the upper part 196 but does not adhere to that surface. Regular cleaning of the upper (smooth) part of the percutaneous portion 180 may be performed to ensure no tissue adheres thereto. This arrangement ensures the port unit is not marsupialised and also reduces the risk of infection.

It is important to note that many other techniques or variants of the above described technique may be used to form port units as described herein. In particular, the skilled person would be aware of the various ways in which such port units could be manufactured in a reliable and cost effective manner.

Figure 6:
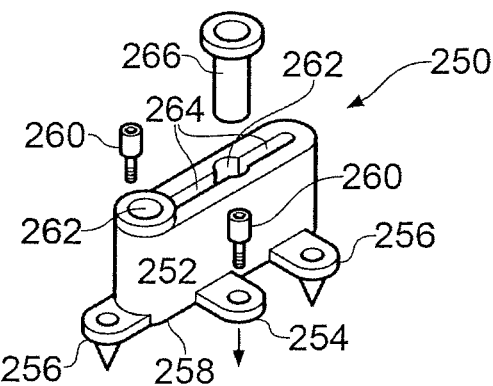
FIG. 6 shows a guide device for implanting the drug delivery port shown in FIGS. 1 to 5, FIGS. 7*a*-7*g* show a surgical technique for implanting the neurological drug delivery apparatus of FIG. 1.

FIG. 6 shows an implantation aid 250 that is designed to facilitate implantation of the above described port units (e.g. a port unit 10 or 110). The implantation aid 250 comprises an oval metal block 252 having a pair of flanges 254 and a plurality of bone pins 256 provided at a lower (skull facing) surface 258. The implantation aid 250 can thus be temporarily affixed to skull by bone screws 260 passed through holes in the flanges 254. The metal block 252 also includes a pair of drill guide holes 262 that can receive removable drill hole sleeves 266 and an interconnecting metal slot 264. The dimensions and spacing of the drill hole sleeves, guide holes 262 and slot 264 correspond to the dimensions of the port unit that is to be attached to the skull. As will be described below, the implantation aid 250 allows the skull to be cut using cutting tools so as to form a recess that is shaped to receive the subcutaneous portion of the port unit.

Referring to FIGS. 7a to 7g, a surgical method will be described for implanting neurological apparatus comprising a port unit and a router unit as described with reference to FIGS. 1-3 using the implantation aid described with reference to FIG. 6.

Figure 7A:
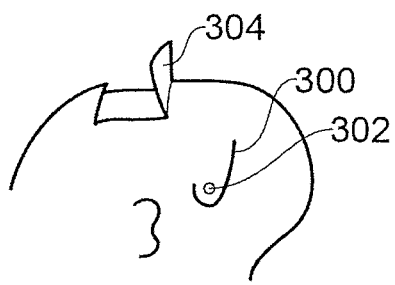
Figure 7B:
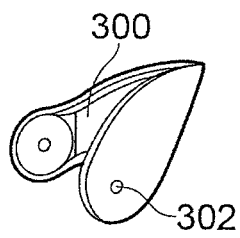

FIG. 7a shows a first step in the method of marking out a flap 300 behind the ear of a subject using a template. The scalp is also punctured at position 302 in a manner that marks the skull bone. A larger flap 304 is also made at the site where the catheter burr holes and router unit are to be located. FIG. 7b shows the flap 300 after being turned over. The subdermal tissue is also removed at this stage.

Figure 7C:
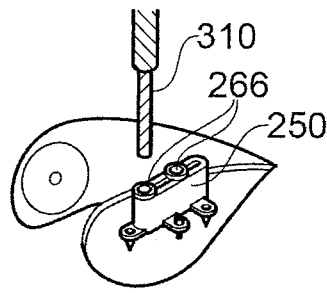

FIG. 7c illustrates the implantation aid 250 described with reference to FIG. 6 attached to the skull by bone screws 260. The alignment aid 250 is located in position using the puncture mark made in the skull as reference mark. The drill hole sleeves 266 are placed in the drill guide holes 262 and a drill 310 is passed through each of the holes in turn to form two holes in the skull. Each drilled hole has a depth of around 5 mm.

Figure 7D:
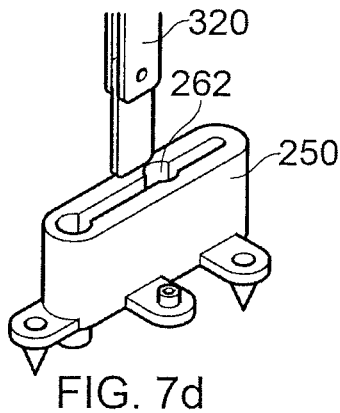
Figure 7E:
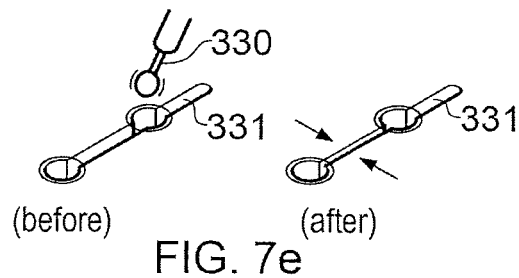

FIG. 7d shows the step, which is performed after removing the drill hole sleeves 266 from the drill guide holes 262, of cutting an approximately 1 mm wide trench using an oscillating saw 320. The implantation aid 250 is then detached from the skull. FIG. 7e shows the next step of using a 2 mm burr device 330 to widen the distal slot 331 to approximately 2 mm.

Figure 7F:
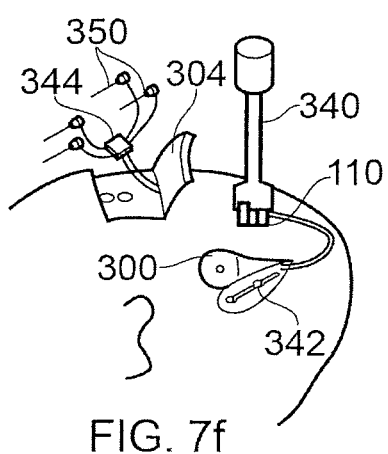

FIG. 7f then shows the step of using an impactor 340, to which a port unit 110 as described with reference to FIG. 4 is attached, to tap that port unit 110 into a snug engagement with the appropriately shaped hole 342 in the skull. A router unit 344 and catheters 350 can also be implanted at this stage.

Figure 7G:
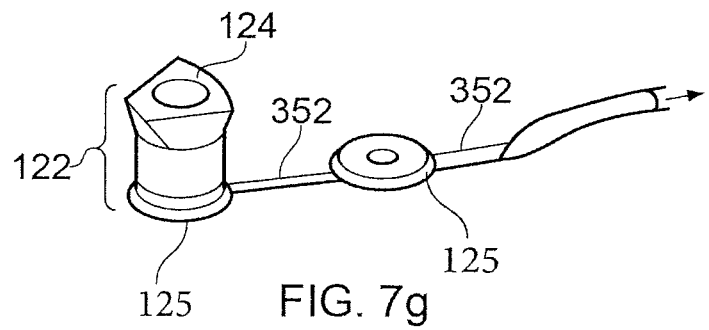

Finally, as shown in FIG. 7g, the impactor 340 is disconnected from the port unit 110 and the slots 352 are backfilled with bone chippings. It can then be seen that the subcutaneous portion 120 of the port unit 110 is buried substantially within the skull bone and that the percutaneous portion 122 will protrude through the skin of the scalp to provide the extracorporeal surface 124.

The above described surgical implantation method is merely one example of how the port unit could be surgically implanted and the skilled person would appreciate that numerous variations of the above method are possible. For example, a linear incision or an L-shaped (hockey stick) incision could be made in the skin instead of forming a skin flap as described above. The skin could then be thinned on either side of the incision and enough skin removed to accommodate the percutaneous portion 180 of the port unit. The port unit may also be mounted to other areas of the head or to a different bone in the body. For example, the port unit could be mounted to the sternum if delivery of therapeutic agents to the spinal cord was required. It would also be possible to mount the device within the mouth (e.g. to the jaw bone). A mouth mounted device may take the form of a (e.g. ceramic) tooth or pass through a tooth.

The examples described above with reference to FIGS. 1 to 7 describe port units that comprise two substantially cylindrical parts joined by an elongate joining section. Such port units can be securely affixed to the skull and provide a barrier to infection reaching the implanted catheter device from the percutaneous part of the port unit.

Figure 8:
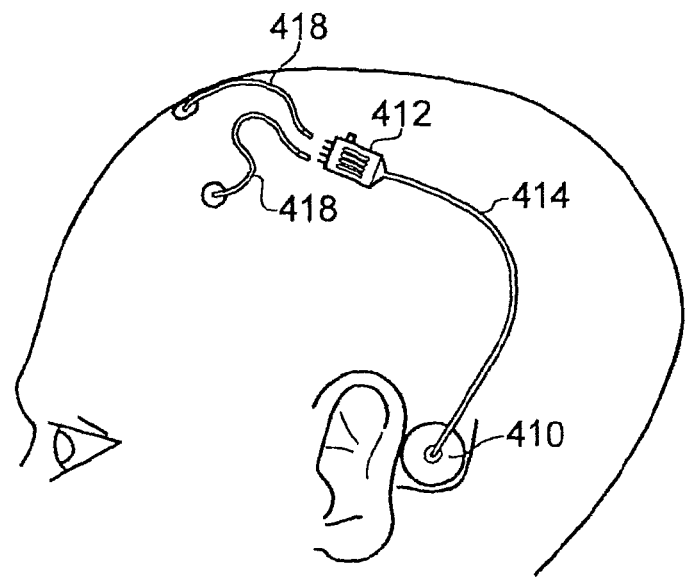
FIG. 8 illustrates a further implantable neurological drug delivery apparatus of the present invention.

FIG. 8 illustrates neurological apparatus comprising a port unit 410 connected to a router unit 412 by a four lumen supply tube 414. Intraparenchymal catheter devices 418 are connected to the router unit 412. The router unit 412 also comprises a bacterial filter.

Figure 9A:
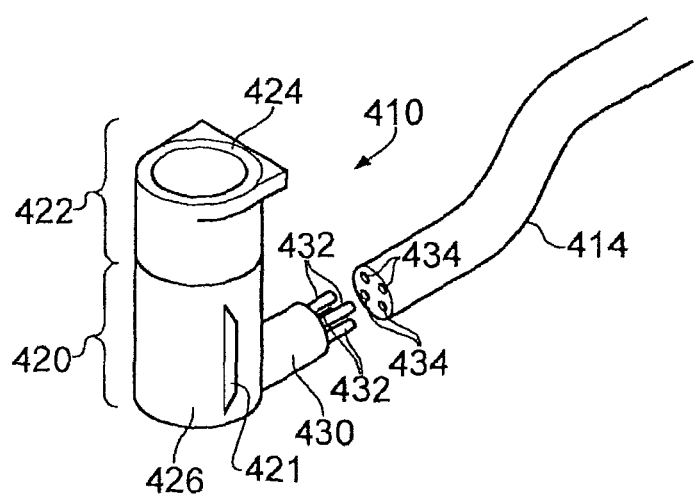
FIGS. 9*a*-9*c* show in more detail the percutaneous drug delivery port of the apparatus of FIG. 8, FIG. 10 show a further implantable neurological drug delivery apparatus of the present invention

Referring to FIG. 9a, the port unit 410 that is illustrated in FIG. 8 is shown in more detail. The port unit 410 comprises a subcutaneous portion 420 and a percutaneous portion 422 that has an extracorporeal surface 424. The subcutaneous portion 420 comprises a plurality of protruding broaching fins 421 that run along the majority of its length. The subcutaneous portion 420 also comprises a first substantially cylindrical part 426 from which an elongate section 430 protrudes. The distal end of the elongate section 430 comprises four protruding rigid tubes 432 for engaging and providing a separate fluidic link with each of the four lumens 434 of the supply tube 414. The percutaneous portion 422 include a rubber bung accessible from the extracorporeal surface 424 that seals four separate fluidic channels through the port unit 410. Insertion of fluid delivery needles through the rubber bung provides fluid access to the separate fluidic channels of the port unit thereby permitting fluid to be pumped to attached catheter devices via the supply tube 414 and router unit 412.

Figure 9B:
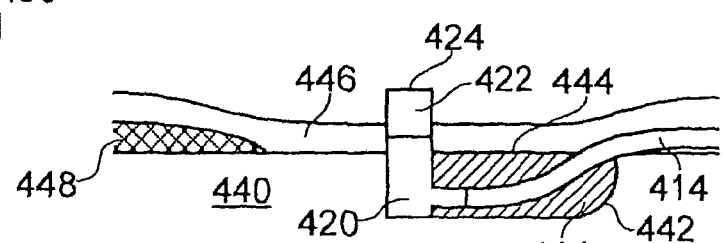
Figure 9C:
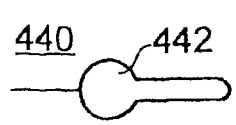

FIG. 9b shows a side view of the port unit 410 implanted in a key shaped recess 442 as shown in FIG. 9c that is formed in the skull bone 440 of a subject. Implantation may be performed by forcing the port unit 410 into the recess using an impactor or the like, thereby causing the fins 421 to cut into the bone and thus affixing the port unit in place. The key-like shape of the port unit in combination with the fins 421 acts to secure the port unit 410 in place and prevents any unwanted movement (e.g. rotation) thereof. The majority of the subcutaneous portion 422 is located below the outer surface of the skull bone 440 whilst the percutaneous portion 422 passes through a hole in the skin. The elongate section 430 of the port unit 410 and the proximal end of the supply tube 414 are also buried below the outer surface of the skull in an aperture that is back filled with bone chippings 444. The dermis of the skin 446 seals against the roughened surfaces of the subcutaneous portion 422 and percutaneous portion 422. It is also noted that the hypodermis or subdermal tissue 448 is thinned in the region of port unit implantation thereby allowing a living seal to be provided between the dermis and the periosteum.

It should also be noted that it would be possible to integrate the supply tube 414 with the elongate section 430 of the port unit 410. For example, the proximal end of a supply tube could protrude directly from the first substantially cylindrical part 426 to form the buried elongate section of the subcutaneous portion 422.

Figure 10:
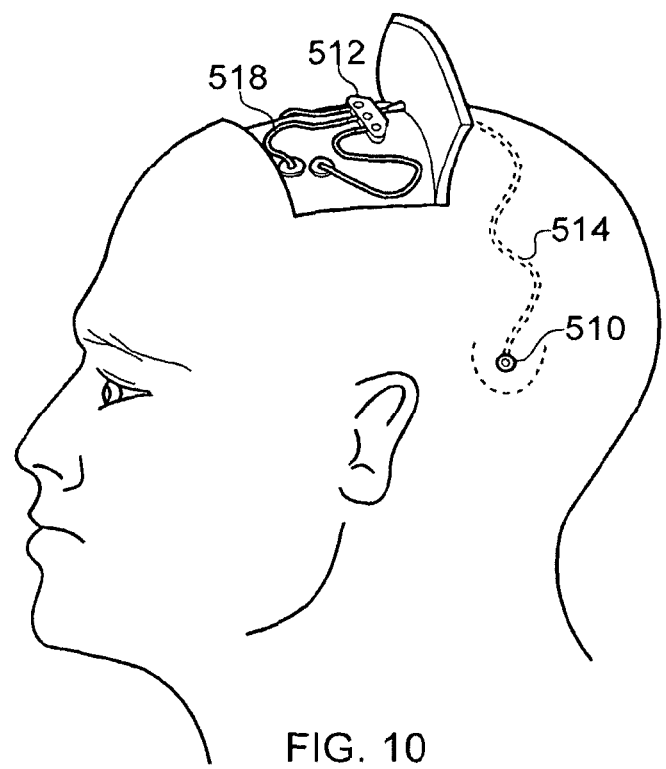
Figure 11:
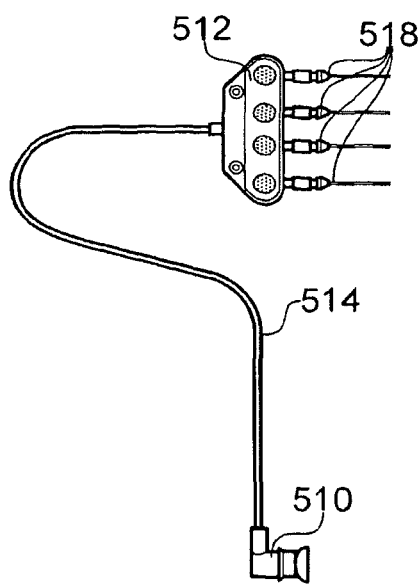
FIG. 11 shows the air/bacterial filter and percutaneous drug delivery port of the apparatus of FIG. 10.
Figure 12:
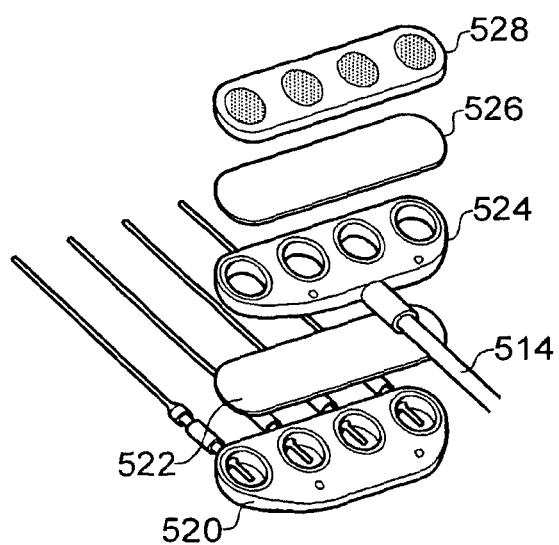
FIG. 12 is an exploded view of the air/bacterial filter shown in FIGS. 10 and 11.

FIGS. 10 to 12 show further neurological apparatus that comprises a port unit 510, a supply tube 514, a router unit 512 and four catheter devices 518. In particular, FIG. 10 shows the apparatus implanted in a subject, FIG. 11 illustrates the apparatus prior to implantation and FIG. 12 show the components of the filter unit in more detail.

Referring to FIGS. 10 and 11, it can be seen how the port unit 510 is connected to the router unit 512 by the supply tube 514. The catheter devices 518 are each linked to an outlet of the router unit. The port unit 510 is analogous to the port unit 410 described above with reference to FIGS. 8 and 9a-9c. The router unit 512, however, provides an air filtering function.

Referring to FIG. 12, the structure of the router unit 512 is shown in more detail. The router unit 512 comprises a four chamber outflow portion 520, a hydrophilic (bacterial) filter 522, a four chamber inflow portion 524, a hydrophobic filter 526 and a diaphragm membrane 528. As described in more detail below, fluid passed to the router unit 512 through the four lumens of the supply tube 514 is separately filtered and output via outlets 530 to the respective catheter devices 518. In other words, each fluid path through the router unit is separately filtered and there is no mixing of the fluid that is routed to the different catheter devices 518.

In operation, fluid from each lumen of the supply tube 514 passes to a respective one of the inflow chambers of the inflow portion 524. The liquid of the fluid is attracted to the hydrophilic filter 522 and passes through that hydrophilic filter 522 into the associated outflow chamber of the outflow portion 520. Gas (e.g. air) does not pass through the hydrophilic filter 522. Fluid from each chamber of the outflow portion 520 passes to an outlet 530 that is in turn connected to a catheter device 518. The hydrophobic filter 526 acts as a barrier to liquid, but allows any gas (e.g. air) bubbles to pass through it. Gas (e.g. air) is thus removed from the fluid and is allowed to dissipate through the diaphragm membrane 528 into the body. The hydrophilic filter 522 may also be configured to provide a bacterial filtration function.

As can be seen from FIG. 10, the router unit 512 is located as close to the catheter devices 518 as possible. This ensures air removal is performed as far downstream as possible thereby minimising the amount of air that is present in the fluid expelled from the catheter devices 518. In particular, the air filtration is performed away from the port unit 510 and the majority of the tube connections that could introduce air.

Figure 13:
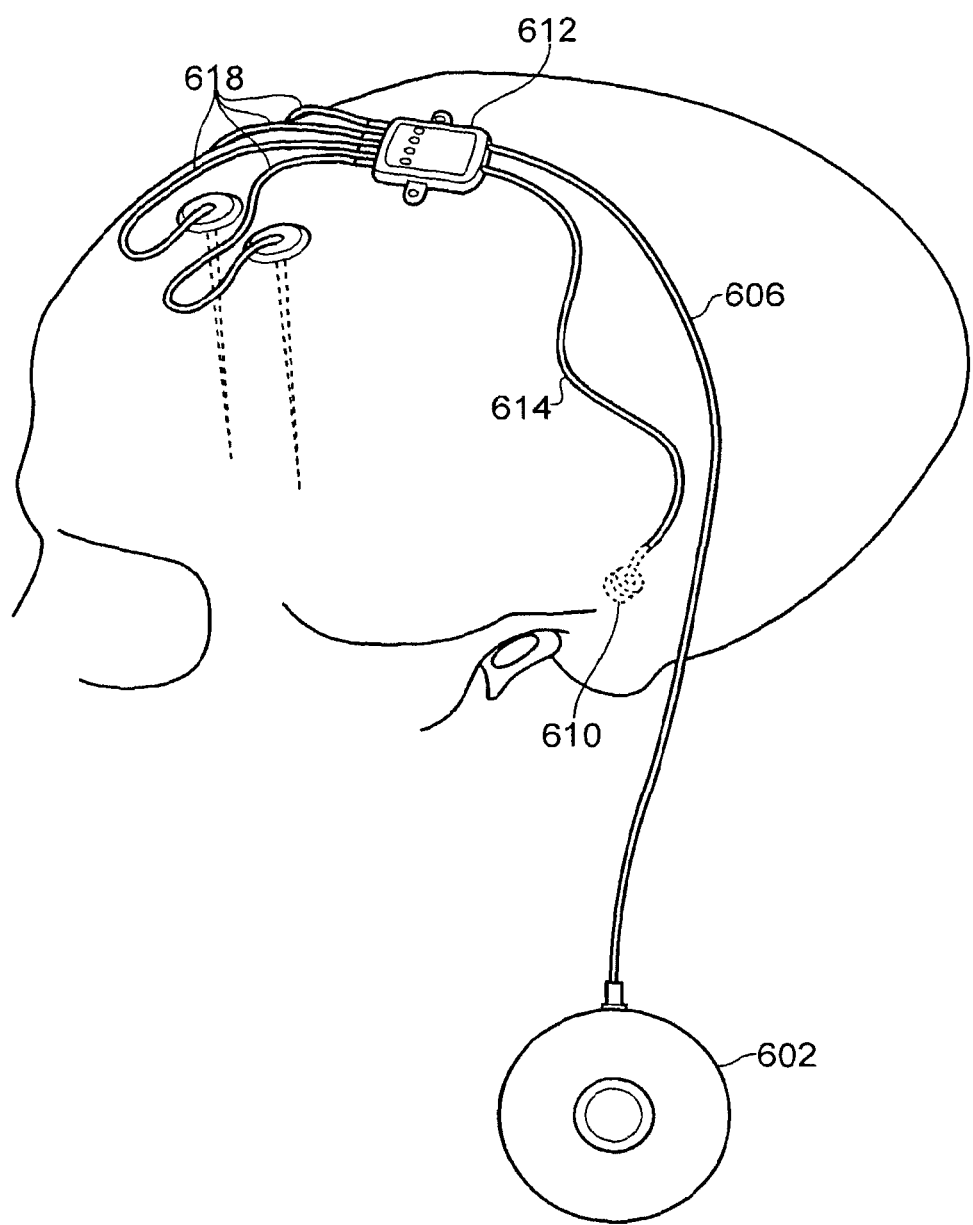
FIG. 13 shows a further implantable neurological drug delivery apparatus of the present invention.

Referring to FIG. 13, a further embodiment of neurological apparatus of the present invention is shown. The apparatus comprises an abdominally implantable constant pressure pump 602, a percutaneous port unit 610, a router unit 612 and catheter device 618. A single lumen supply tube 606 supplies carrier fluid from the pump 602 to the router unit 612. A four lumen supply tube 614 provide four separate fluid pathways from the port unit 610 to the router unit 612. The port unit 610 is preferably a port unit of the type described with reference to FIG. 4. The apparatus is arranged so that a flow of fluid supplied by the abdominal pump 602 is continuously pumped, at a low flow rate, to the catheter devices 618 to prevent occlusion of such devices. Fluid containing a therapeutic agent may also be pumped into the port unit 610 and directed to each catheter device 618 via the router unit 612. The router unit 612 includes a bacterial filter and/or an air filter.

Figure 14:
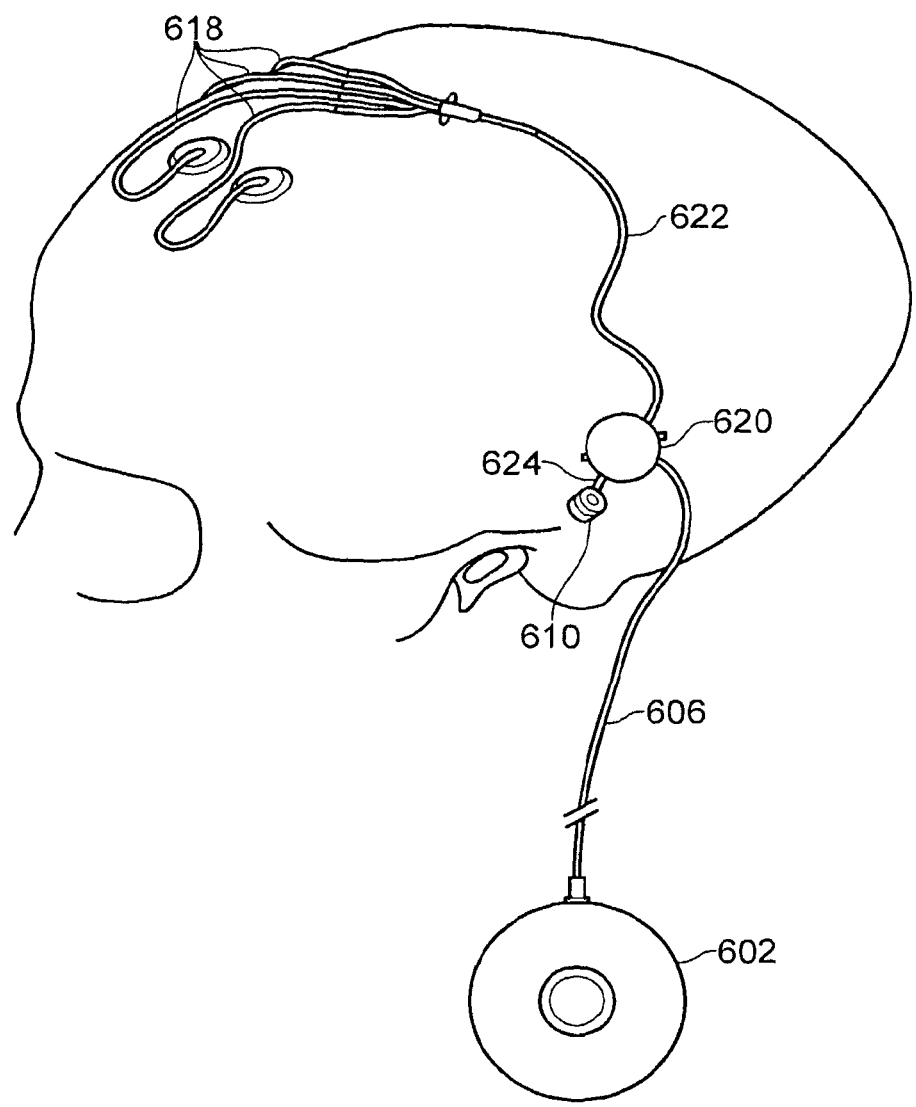
FIG. 14 illustrates a further implantable neurological drug delivery apparatus of the present invention having a separate filter unit.

FIG. 14 illustrates a variant of the device described with reference to FIG. 13. Carrier fluid from an abdominal pump 602 is pumped to a filter unit 620 via a single lumen supply tube 606. The filter unit 620 splits the received carrier fluid into four streams that are routed into the four lumens at the proximal end of the supply tube 622. At the distal end of the supply tube 622, the four lumens separate into four separate tubes that are each connected to a catheter device 618. The port unit 610 is connected to the filter unit 620 by a four lumen supply tube 624 and provides four separate fluidic links to the four separate fluid streams through the filter unit 620. Therapeutic agent may thus be pumped to any one of the catheter devices 618 from the port unit 610.

FIG. 15 illustrates an alternative arrangement to that shown in FIG. 13. Instead of an abdominal pump being used to supply a constant flow of carrier fluid, a ventricular shunt 640 and pump 642 are instead provided. In this arrangement, a constant flow of cerebrospinal fluid (CSF) is passed to the router unit 612 instead of a supply of carrier fluid.

The above described percutaneous fluid port devices can be press fitted into appropriate recesses form in the skull. A number of alternative anchoring arrangement may be used to affix a port units to the skull bone.

FIGS. 16 and 17 illustrate a port unit 710 having a protruding cylindrical portion 712 that engages a complimentary recess 714 formed in a bone 716. As shown in the upper inset of FIG. 16, the cylindrical portion 712 includes perforations 718. As shown in the lower inset of FIG. 16, a complementary circular trench or recess 714 may be formed in the bone, optionally including a central circular island 720. If a circular hole is formed (i.e. without the central circular island 720) bone chippings may be used to fill the internal cavity of the cylindrical portion 712. FIG. 17 illustrates the device of FIG. 16 when fixed in place. Again, the port unit 710 has an extracorporeal surface 724 that allows access to ports or fluid channels that exit the unit subcutaneously.

Supply tubing 730 may be routed through a slot formed in the cylindrical portion 712. Such supply tubing 730 may be buried, at least partially, within a trench formed in the bone. For example, the proximal end of the supply tubing 730 may form an elongate section that is buried in the bone in a similar manner to that described above.

Figure 18:
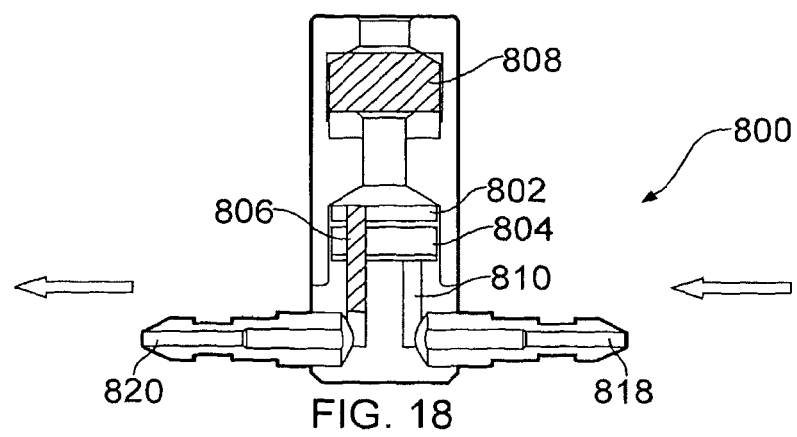
FIG. 18 shows a valved percutaneous drug delivery port.
Figure 19:
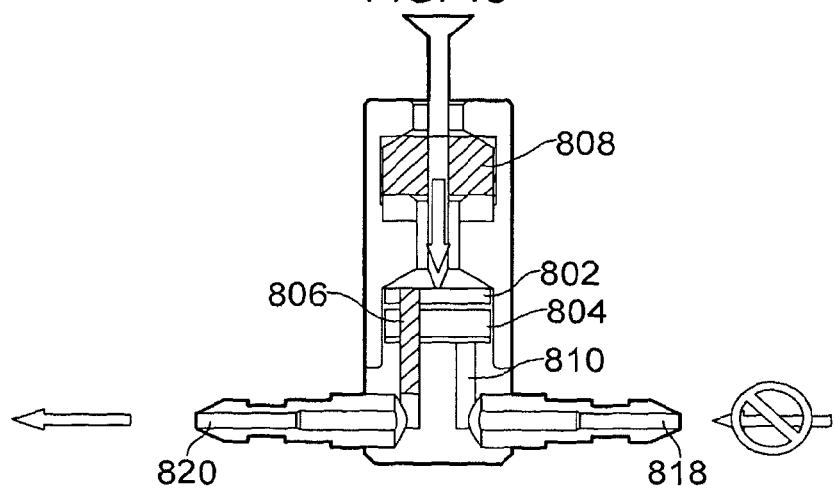
FIG. 19 shows the valved percutaneous drug delivery port of FIG. 18 with a needle for delivering therapeutic agent inserted.
Figure 20:
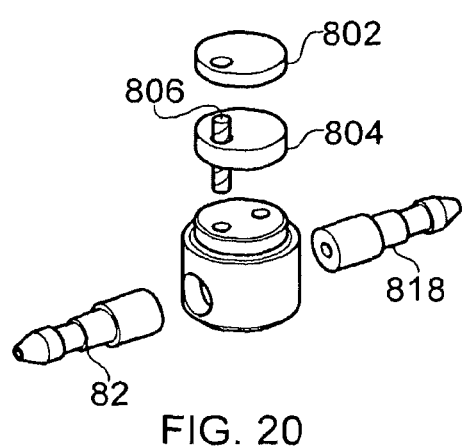
FIG. 20 is an exploded view of the valved percutaneous drug delivery port shown in FIGS. 18 and 19.

Referring next to FIGS. 18 to 20, a variant of the port described above with reference to FIGS. 1 to 3 is shown.

FIG. 18 is a cross-section showing the components of the valved port unit 800. The valved port unit 800 comprises a washer 802 and gasket 804 that are constrained by a hypotube 806 but are otherwise free to move within the cavity. A septum 808 is also provided. The port unit 800 is shown in FIG. 18 when in a first state that allows fluid to flow from the inlet 818 to the outlet 820. In particular, it can be seen that without the gasket 804 blocking the inlet channel 810, liquid received under pressure at the inlet 818 can flow to the outlet 820.

FIG. 19 shows the valved port unit 800 when a hollow needle 830 is inserted through the septum 808 thereby pushing down on the washer 802. In this second state, the washer 802 compresses the gasket 804 thereby blocking the egress of fluid from the inlet channel 810. The fluid path from the inlet 818 to the outlet 820 is thus obstructed. Instead, fluid dispensed through the inserted needle 830 can be pumped to the outlet 820 and onward to implanted catheter device.

FIG. 20 shows an exploded view of the internal components of the valved port unit 800. The valved port unit 800 may, in common with the port unit described above, have a subcutaneous portion that can be located in a recess formed in bone and a percutaneous portion protruding therefrom.

It should again be remembered that the above examples are merely illustrative of the present invention. Port units having a single port, two ports or four ports are described in detail above, but the invention is equally applicable to port units having a different number of ports. Furthermore, the methods of manufacturing the port units and the way in which they are implanted are merely illustrative. The use of a wide variety of manufacturing and/or implantation techniques would be possible. Furthermore, although the above devices are described for use in delivering fluid into the body, it should be noted that such devices could also be used as shunts for extracting fluid from the body. The percutaneous fluid delivery device described in detail above could thus be used as a percutaneous fluid delivery or fluid extraction device.

The invention claimed is:

1. An implantable percutaneous fluid delivery device comprising:
   a subcutaneous base portion comprising one or more ports configured to supply fluid to one or more implanted catheter devices; and
   a percutaneous portion comprising an extracorporeal surface, the one or more ports of the subcutaneous base portion configured to be accessible from the extracorporeal surface of the percutaneous portion, and at least part of the percutaneous portion comprises a at least one of a peripheral porous surface and a peripheral rough surface configured to encourage tissue ingrowth,
   wherein the subcutaneous base portion is configured to be at least partially insertable into a complementary recess formed in a bone, the subcutaneous base portion comprising at least one bone anchor configured to grip an internal surface of the complementary recess in order to directly secure the subcutaneous base portion to the bone.

2. The device according to claim 1, wherein the at least one bone anchor is configured to enable the subcutaneous base portion to be retained in the complementary recess by a friction fit.

3. The device according to claim 1, wherein the at least one bone anchor comprises one or more protrusions provided on an outer surface of the subcutaneous base portion, the one or more protrusions configured to allow the device to be secured in the complementary recess by a push-fit action.

4. The device according to claim 1, wherein the subcutaneous base portion further comprises at least one of a rough surface and a coating configured to promote osseointegration.

5. The device according to claim 1, wherein the subcutaneous base portion comprises a protruding lip.

6. The device according to claim 1, wherein the subcutaneous base portion comprises a first part configured to attach to the percutaneous portion and an elongate section protruding from the first part, wherein, when the percutaneous fluid delivery device is implanted in a body, a whole of the elongate section is located within the complementary recess formed in the bone.

7. The device according to claim 6, wherein the subcutaneous base portion comprises a second part, the first part and the second part being connected by the elongate section.

8. The device according to claim 6, wherein a length of the elongate section is at least 10 mm.

9. The device according to claim 1, wherein the subcutaneous base portion comprises two or more ports.

10. The device according to claim 1, further comprising at least one of a bacterial filter and an air vent.

11. The device according to claim 1, wherein the subcutaneous base portion comprises at least one subcutaneous fluid inlet configured to receive fluid from at least one remotely implanted pump, wherein fluid received at the at least one subcutaneous fluid inlet is routable to the one or more ports.

12. A Neurological apparatus comprising:
an implantable percutaneous fluid delivery device according to claim 1;
a supply tube having one or more lumens;
an implantable router unit having one or more inlets configured to route fluid to one or more outlets; and
one or more intraparenchymal catheter devices,
wherein the one or more ports of the percutaneous fluid delivery device are connected to the one or more inlets of the router unit via the supply tube and the one or more intraparenchymal catheter devices are connected to the one or more outlets of the implantable router unit.

13. The apparatus according to claim 12, further comprising an external fluid connector unit configured to cooperate with the extracorporeal surface of the percutaneous fluid delivery device to provide fluid communication with the ports.

14. A kit for implanting a percutaneous fluid delivery device, the kit comprising:
the implantable percutaneous fluid delivery device of claim 1; and
a jig that provides a template for cutting a recess in bone into which the subcutaneous base portion of the percutaneous fluid delivery device is fitted.

15. The device according to claim 1, wherein the peripheral surface is coated with hydroxyapatite.

16. The device according to claim 1, wherein the peripheral surface is coated with a nano-fibrous matrix.

17. An implantable percutaneous fluid delivery device comprising:
a subcutaneous base portion comprising one or more ports configured to supply fluid to one or more implanted catheter devices; and
a percutaneous portion comprising an extracorporeal surface, the one or more ports of the subcutaneous base portion configured to be accessible from the extracorporeal surface of the percutaneous portion, at least part of the percutaneous portion comprises at least one of a peripheral porous surface and a peripheral rough surface configured to encourage tissue ingrowth,
wherein the subcutaneous base portion is configured to be at least partially insertable into a complementary recess formed in a bone and at least part of the subcutaneous base portion is configured to osseointegrate following implantation.

18. The device according to claim 17, wherein the subcutaneous base portion further comprises at least one of a rough surface and a coating configured to promote osseointegration.

* * * * *